United States Patent [19]
Hashiguchi et al.

[11] Patent Number: 5,998,178
[45] Date of Patent: *Dec. 7, 1999

[54] L-ISOLEUCINE-PRODUCING BACTERIUM AND METHOD FOR PREPARING L-ISOLEUCINE THROUGH FERMENTATION

[75] Inventors: Ken-ichi Hashiguchi; Hiroko Kishino; Nobuharu Tsujimoto; Hiroshi Matsui, all of Kawasaki, Japan

[73] Assignee: Ajinomoto Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/452,075

[22] Filed: May 26, 1995

[30] Foreign Application Priority Data

May 30, 1994 [JP] Japan ..................... 6-116340

[51] Int. Cl.⁶ ............... C12P 13/06; C12N 1/21
[52] U.S. Cl. ........................ 435/116; 435/252.33
[58] Field of Search .................. 435/116, 252.33

[56] References Cited

U.S. PATENT DOCUMENTS

| | | | |
|---|---|---|---|
| 4,278,765 | 7/1981 | Debabov et al. | 435/172.3 |
| 5,175,107 | 12/1992 | Debabov et al. | 435/252.33 |

FOREIGN PATENT DOCUMENTS

| | | |
|---|---|---|
| 2-458 | 5/1990 | Japan . |
| 6-133787 | 5/1994 | Japan . |
| 94/11517 | 5/1994 | WIPO . |

OTHER PUBLICATIONS

Gavrilova et al., Biotekhnologiya 4(5):600–608, 1988.
Lawther et al., Nucleic Acids Res. 15:2137–2155, 1987.
Chen et al., J. Bacteriol. 173:2328–2340, 1991.
Cohen et al., in *Escherichia coli* and *Salmonella typhimurium*: Cellualar and Molecular Biology, Am. Soc. Microbiol., Washington, DC, pp. 429–444, 1987.
WPI 90–047993/07 (JP 2–458), 1990.
WPI 94–183516/22 (WO 94/11517), 1994.
*Biotechnology of Amino Acid Production*, Aida et al Eds., vol. 24, Elsevier, pp. 247–256 (1986).

*Primary Examiner*—Rebecca E. Prouty
*Attorney, Agent, or Firm*—Oblon, Spivak, McClelland, Maier & Neustadt, P.C.

[57] ABSTRACT

An L-isoleucine-producing bacterium belonging to the genus Escherichia which carries a thrABC operon which comprises a thrA gene coding for aspartokinase I-homoserine dehydrogenase I substantially released from the inhibition by L-threonine and an ilvGMEDA operon which comprises an ilvA gene coding for threonine deaminase substantially released from the inhibition by L-isoleucine and whose region required for attenuation is removed; and an L-isoleucine-producing bacterium belonging to the genus Escherichia carrying the thrABC operon, an lysC gene coding for aspartokinase III substantially released from the inhibition by L-lysine, and the ilvGMEDA operon. The bacteria permit biosynthesis of a sufficient amount of L-isoleucine.

16 Claims, 4 Drawing Sheets

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 2841 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 957..1052

(ix) FEATURE:
      (A) NAME/KEY: CDS
      (B) LOCATION: 1195..2838

(xi) SEQUENCE DESCRIPTION: SEQ ID NO:1:

```
CTCGCTTTCC TTGTTCCTGA CCGATAACAT CACTGAGATC ATGTTGTAGC GCCCGGGATA      60

CTGCATCAGT TGGTTTCGGG CGTTCGAGAG CGTGCTTACC TTCCAGAAAC GCACAGACAG     120

CTTGCAGATG ATCGGCTATC AGGCATCCTT CACCGTTAAT TAGCCCCACT TCATCTTCGT     180

TATCTTTCGC GACGATAATT TTTCTGCCCG ACTTAATAGC TTCAGTTGCA CTGGAGATTG     240

CGCCGGGAAC GCCACGCAGA GCGCCTGTAA GCGCCAGTTC TCCGACTAAT TCATATTCAT     300

CTAACTTATT GGCTGTAAGC TGTTCTGAGG CCGCCAGCAA CGCAATGGCG ATAGGTAAAT     360

CATATCGTCC CCCTTCTTTT GGCAGATCAG CTGGAGCCAG GTTGATGGTG ATTTTTTTCG     420

CCGGATATTC ATATCCGCTA TTGATAATGG CGCTGCGCAC GCGATCGCGA GCTTCTTTTA     480

CCGTTGTTTC TGGTAAGCCC ACCATCGTTA AGCCGGGTAG ACCTTTACTG ATATGTACCT     540

CAACAGTGAT CGGGGGCGCA TTTACTCCCA GGGCTGCGCG GGTATGAACA ATTGACAGTG     600

ACATAAGCCC TCCTTGAGTC ACCATTATGT GCATAAGATA TCGCTGCTGT AGCCCGCTAA     660

TTCGTGAATT TTAGTGGCTG ATTCCTGTTT ATTTGTGCAA GTGAAGTTGA GTTGTTCTGG     720
```

```
CGGTGGAATG ATGCTCGCAA AAATGCAGCG GACAAAGGAT GAACTACGAG GAAGGGAACA      780

ACATTCATAC TGAAATTGAA TTTTTTTCAC TCACTATTTT ATTTTTAAAA AACAACAATT      840

TATATTGAAA TTATTAAACG CATCATAAAA ATCGGCCAAA AAATATCTTG TACTATTTAC      900

AAAACCTATG GTAACTCTTT AGGCATTCCT TCGAACAAGA TGCAAGAAAA GACAAA          956

ATG ACA GCC CTT CTA CGA GTG ATT AGC CTG GTC GTG ATT AGC GTG GTG     1004
Met Thr Ala Leu Leu Arg Val Ile Ser Leu Val Val Ile Ser Val Val
 1               5                  10                  15

GTG ATT ATT ATC CCA CCG TGC GGG GCT GCA CTT GGA CGA GGA AAG GCT     1052
Val Ile Ile Ile Pro Pro Cys Gly Ala Ala Leu Gly Arg Gly Lys Ala
                20                  25                  30

TAGAGATCAA GCCTTAACGA ACTAAGACCC CCGCACCGAA AGGTCCGGGG GTTTTTTTTG     1112

ACCTTAAAAA CATAACCGAG GAGCAGACAA TGAATAACAG CACAAAATTC TGTTTCTCAA     1172

GATTCAGGAC GGGGAACTAA CT ATG AAT GGC GCA CAG TGG GTG GTA CAT GCG     1224
                         Met Asn Gly Ala Gln Trp Val Val His Ala
                          1               5                  10

TTG CGG GCA CAG GGT GTG AAC ACC GTT TTC GGT TAT CCG GGT GGC GCA     1272
Leu Arg Ala Gln Gly Val Asn Thr Val Phe Gly Tyr Pro Gly Gly Ala
                15                  20                  25

ATT ATG CCG GTT TAC GAT GCA TTG TAT GAC GGC GGT GTG GAG CAC TTG     1320
Ile Met Pro Val Tyr Asp Ala Leu Tyr Asp Gly Gly Val Glu His Leu
                30                  35                  40

CTA TGC CGA CAT GAG CAG GGT GCG GCA ATG GCG GCT ATC GGT TAT GCT     1368
Leu Cys Arg His Glu Gln Gly Ala Ala Met Ala Ala Ile Gly Tyr Ala
                45                  50                  55

CGT GCT ACC GGC AAA ACT GGC GTA TGT ATC GCC ACG TCT GGT CCG GGC     1416
Arg Ala Thr Gly Lys Thr Gly Val Cys Ile Ala Thr Ser Gly Pro Gly
         60                  65                  70

GCA ACC AAC CTG ATA ACC GGG CTT GCG GAC GCA CTG TTA GAT TCC ATC     1464
Ala Thr Asn Leu Ile Thr Gly Leu Ala Asp Ala Leu Leu Asp Ser Ile
 75                  80                  85                  90

CCT GTT GTT GCC ATC ACC GGT CAA GTG TCC GCA CCG TTT ATC GGC ACT     1512
Pro Val Val Ala Ile Thr Gly Gln Val Ser Ala Pro Phe Ile Gly Thr
                 95                 100                 105

GAC GCA TTT CAG GAA GTG GAT GTC CTG GGA TTG TCG TTA GCC TGT ACC     1560
Asp Ala Phe Gln Glu Val Asp Val Leu Gly Leu Ser Leu Ala Cys Thr
                110                 115                 120

AAG CAT AGC TTT CTG GTG CAG TCG CTG GAA GAG TTG CCG CGC ATC ATG     1608
Lys His Ser Phe Leu Val Gln Ser Leu Glu Glu Leu Pro Arg Ile Met
        125                 130                 135

GCT GAA GCA TTC GAC GTT GCC TGC TCA GGT CGT CCT GGT CCG GTT CTG     1656
Ala Glu Ala Phe Asp Val Ala Cys Ser Gly Arg Pro Gly Pro Val Leu
 140                 145                 150

GTC GAT ATC CCA AAA GAT ATC CAG TTA GCC AGC GGT GAC CTG GAA CCG     1704
Val Asp Ile Pro Lys Asp Ile Gln Leu Ala Ser Gly Asp Leu Glu Pro
155                 160                 165                 170

TGG TTC ACC ACC GTT GAA AAC GAA GTG ACT TTC CCA CAT GCC GAA GTT     1752
Trp Phe Thr Thr Val Glu Asn Glu Val Thr Phe Pro His Ala Glu Val
                175                 180                 185

GAG CAA GCG CGC CAG ATG CTG GCA AAA GCG CAA AAA CCG ATG CTG TAC     1800
Glu Gln Ala Arg Gln Met Leu Ala Lys Ala Gln Lys Pro Met Leu Tyr
                190                 195                 200

GTT GGC GGT GGC GTG GGT ATG GCG CAG GCA GTT CCG GCT TTG CGT GAA     1848
Val Gly Gly Gly Val Gly Met Ala Gln Ala Val Pro Ala Leu Arg Glu
        205                 210                 215

TTT CTC GCT GCC ACA AAA ATG CCT GCC ACC TGT ACG CTG AAA GGG CTG     1896
Phe Leu Ala Ala Thr Lys Met Pro Ala Thr Cys Thr Leu Lys Gly Leu
 220                 225                 230
```

```
GGC GCA GTA GAA GCA GAT TAT CCG TAC TAT CTG GGC ATG CTG GGG ATG    1944
Gly Ala Val Glu Ala Asp Tyr Pro Tyr Tyr Leu Gly Met Leu Gly Met
235                 240                 245                 250

CAC GGC ACC AAA GCG GCA AAC TTC GCG GTG CAG GAG TGT GAC CTG CTG    1992
His Gly Thr Lys Ala Ala Asn Phe Ala Val Gln Glu Cys Asp Leu Leu
                255                 260                 265

ATC GCC GTG GGC GCA CGT TTT GAT GAC CGG GTG ACC GGC AAA CTG AAC    2040
Ile Ala Val Gly Ala Arg Phe Asp Asp Arg Val Thr Gly Lys Leu Asn
            270                 275                 280

ACC TTC GCG CCA CAC GCC AGT GTT ATC CAT ATG GAT ATC GAC CCG GCA    2088
Thr Phe Ala Pro His Ala Ser Val Ile His Met Asp Ile Asp Pro Ala
        285                 290                 295

GAA ATG AAC AAG CTG CGT CAG GCA CAT GTG GCA TTA CAA GGT GAT TTA    2136
Glu Met Asn Lys Leu Arg Gln Ala His Val Ala Leu Gln Gly Asp Leu
300                 305                 310

AAT GCT CTG TTA CCA GCA TTA CAG CAG CCG TTA AAT CAA TGT GAC TGG    2184
Asn Ala Leu Leu Pro Ala Leu Gln Gln Pro Leu Asn Gln Cys Asp Trp
315                 320                 325                 330

CAG CAA CAC TGC GCG CAG CTG CGT GAT GAA CAT TCC TGG CGT TAC GAC    2232
Gln Gln His Cys Ala Gln Leu Arg Asp Glu His Ser Trp Arg Tyr Asp
                335                 340                 345

CAT CCC GGT GAC GCT ATC TAC GCG CCG TTG TTG TTA AAA CAA CTG TCG    2280
His Pro Gly Asp Ala Ile Tyr Ala Pro Leu Leu Leu Lys Gln Leu Ser
            350                 355                 360

GAT CGT AAA CCT GCG GAT TGC GTC GTG ACC ACA GAT GTG GGG CAG CAC    2328
Asp Arg Lys Pro Ala Asp Cys Val Val Thr Thr Asp Val Gly Gln His
        365                 370                 375

CAG ATG TGG GCT GCG CAG CAC ATC GCC CAC ACT CGC CCG GAA AAT TTC    2376
Gln Met Trp Ala Ala Gln His Ile Ala His Thr Arg Pro Glu Asn Phe
380                 385                 390

ATC ACC TCC AGC GGT TTA GGT ACC ATG GGT TTT GGT TTA CCG GCG GCG    2424
Ile Thr Ser Ser Gly Leu Gly Thr Met Gly Phe Gly Leu Pro Ala Ala
395                 400                 405                 410

GTT GGC GCA CAA GTC GCG CGA CCG AAC GAT ACC GTT GTC TGT ATC TCC    2472
Val Gly Ala Gln Val Ala Arg Pro Asn Asp Thr Val Val Cys Ile Ser
                415                 420                 425

GGT GAC GGC TCT TTC ATG ATG AAT GTG CAA GAG CTG GGC ACC GTA AAA    2520
Gly Asp Gly Ser Phe Met Met Asn Val Gln Glu Leu Gly Thr Val Lys
            430                 435                 440

CGC AAG CAG TTA CCG TTG AAA ATC GTC TTA CTC GAT AAC CAA CGG TTA    2568
Arg Lys Gln Leu Pro Leu Lys Ile Val Leu Leu Asp Asn Gln Arg Leu
        445                 450                 455

GGG ATG GTT CGA CAA TGG CAG CAA CTG TTT TTT CAG GAA CGA TAC AGC    2616
Gly Met Val Arg Gln Trp Gln Gln Leu Phe Phe Gln Glu Arg Tyr Ser
460                 465                 470

GAA ACC ACC CTT ACT GAT AAC CCC GAT TTC CTC ATG TTA GCC AGC GCC    2664
Glu Thr Thr Leu Thr Asp Asn Pro Asp Phe Leu Met Leu Ala Ser Ala
475                 480                 485                 490

TTC GGC ATC CAT GGC CAA CAC ATC ACC CGG AAA GAC CAG GTT GAA GCG    2712
Phe Gly Ile His Gly Gln His Ile Thr Arg Lys Asp Gln Val Glu Ala
                495                 500                 505

GCA CTC GAC ACC ATG CTG AAC AGT GAT GGG CCA TAC CTG CTT CAT GTC    2760
Ala Leu Asp Thr Met Leu Asn Ser Asp Gly Pro Tyr Leu Leu His Val
            510                 515                 520

TCA ATC GAC GAA CTT GAG AAC GTC TGG CCG CTG GTG CCG CCT GGC GCC    2808
Ser Ile Asp Glu Leu Glu Asn Val Trp Pro Leu Val Pro Pro Gly Ala
        525                 530                 535

AGT AAT TCA GAA ATG TTG GAG AAA TTA TCA TGA                        2841
Ser Asn Ser Glu Met Leu Glu Lys Leu Ser
540                 545
```

(2) INFORMATION FOR SEQ ID NO:2:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Ala Leu Leu Arg Val Ile Ser Leu Val Val Ile Ser Val Val
 1               5                  10                  15

Val Ile Ile Ile Pro Pro Cys Gly Ala Ala Leu Gly Arg Gly Lys Ala
                20                  25                  30
```

(2) INFORMATION FOR SEQ ID NO:3:

(i) SEQUENCE CHARACTERISTICS:
        (A) LENGTH: 548 amino acids
        (B) TYPE: amino acid
        (D) TOPOLOGY: linear (ii) MOLECULE TYPE: protein (xi) SEQUENCE DESCRIPTION: SEQ ID NO:3:

```
Met Asn Gly Ala Gln Trp Val Val His Ala Leu Arg Ala Gln Gly Val
 1               5                  10                  15

Asn Thr Val Phe Gly Tyr Pro Gly Gly Ala Ile Met Pro Val Tyr Asp
                20                  25                  30

Ala Leu Tyr Asp Gly Gly Val Glu His Leu Leu Cys Arg His Glu Gln
                35                  40                  45

Gly Ala Ala Met Ala Ala Ile Gly Tyr Ala Arg Ala Thr Gly Lys Thr
 50                  55                  60

Gly Val Cys Ile Ala Thr Ser Gly Pro Gly Ala Thr Asn Leu Ile Thr
 65                  70                  75                  80

Gly Leu Ala Asp Ala Leu Leu Asp Ser Ile Pro Val Val Ala Ile Thr
                85                  90                  95

Gly Gln Val Ser Ala Pro Phe Ile Gly Thr Asp Ala Phe Gln Glu Val
                100                 105                 110

Asp Val Leu Gly Leu Ser Leu Ala Cys Thr Lys His Ser Phe Leu Val
                115                 120                 125

Gln Ser Leu Glu Glu Leu Pro Arg Ile Met Ala Glu Ala Phe Asp Val
 130                 135                 140

Ala Cys Ser Gly Arg Pro Gly Pro Val Leu Val Asp Ile Pro Lys Asp
145                 150                 155                 160

Ile Gln Leu Ala Ser Gly Asp Leu Glu Pro Trp Phe Thr Thr Val Glu
                165                 170                 175

Asn Glu Val Thr Phe Pro His Ala Glu Val Glu Gln Ala Arg Gln Met
                180                 185                 190

Leu Ala Lys Ala Gln Lys Pro Met Leu Tyr Val Gly Gly Gly Val Gly
                195                 200                 205

Met Ala Gln Ala Val Pro Ala Leu Arg Glu Phe Leu Ala Ala Thr Lys
 210                 215                 220

Met Pro Ala Thr Cys Thr Leu Lys Gly Leu Gly Ala Val Glu Ala Asp
225                 230                 235                 240

Tyr Pro Tyr Tyr Leu Gly Met Leu Gly Met His Gly Thr Lys Ala Ala
                245                 250                 255

Asn Phe Ala Val Gln Glu Cys Asp Leu Leu Ile Ala Val Gly Ala Arg
                260                 265                 270
```

Phe Asp Asp Arg Val Thr Gly Lys Leu Asn Thr Phe Ala Pro His Ala
            275                 280                 285

Ser Val Ile His Met Asp Ile Asp Pro Ala Glu Met Asn Lys Leu Arg
            290                 295                 300

Gln Ala His Val Ala Leu Gln Gly Asp Leu Asn Ala Leu Leu Pro Ala
305                 310                 315                 320

Leu Gln Gln Pro Leu Asn Gln Cys Asp Trp Gln His Cys Ala Gln
                325                 330                 335

Leu Arg Asp Glu His Ser Trp Arg Tyr Asp His Pro Gly Asp Ala Ile
            340                 345                 350

Tyr Ala Pro Leu Leu Leu Lys Gln Leu Ser Asp Arg Lys Pro Ala Asp
            355                 360                 365

Cys Val Val Thr Thr Asp Val Gly Gln His Gln Met Trp Ala Ala Gln
            370                 375                 380

His Ile Ala His Thr Arg Pro Glu Asn Phe Ile Thr Ser Ser Gly Leu
385                 390                 395                 400

Gly Thr Met Gly Phe Gly Leu Pro Ala Ala Val Gly Ala Gln Val Ala
                405                 410                 415

Arg Pro Asn Asp Thr Val Val Cys Ile Ser Gly Asp Gly Ser Phe Met
            420                 425                 430

Met Asn Val Gln Glu Leu Gly Thr Val Lys Arg Lys Gln Leu Pro Leu
            435                 440                 445

Lys Ile Val Leu Leu Asp Asn Gln Arg Leu Gly Met Val Arg Gln Trp
            450                 455                 460

Gln Gln Leu Phe Phe Gln Glu Arg Tyr Ser Glu Thr Thr Leu Thr Asp
465                 470                 475                 480

Asn Pro Asp Phe Leu Met Leu Ala Ser Ala Phe Gly Ile His Gly Gln
                485                 490                 495

His Ile Thr Arg Lys Asp Gln Val Glu Ala Ala Leu Asp Thr Met Leu
            500                 505                 510

Asn Ser Asp Gly Pro Tyr Leu Leu His Val Ser Ile Asp Glu Leu Glu
            515                 520                 525

Asn Val Trp Pro Leu Val Pro Pro Gly Ala Ser Asn Ser Glu Met Leu
530                 535                 540

Glu Lys Leu Ser
545

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

TAACATCACT GAGATCATGT TG                                                22

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid -continued (xi) SEQUENCE DESCRIPTION: SEQ ID NO:5:

TCTTTTCTTG CATCTTGTTC G                                                    21

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

TCTGTTTCTC AAGATTCAGG AC                                                   22

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

CGCCGGTAAA CCAAAACCC                                                       19

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

CTTCCCTTGT GCCAAGGCTG                                                      20

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

GAATTCCTTT GCGAGCAG                                                        18

L-ISOLEUCINE-PRODUCING BACTERIUM AND METHOD FOR PREPARING L-ISOLEUCINE THROUGH FERMENTATION

BACKGROUND OF THE INVENTION

The present invention relates to a method for preparing, through fermentation, L-isoleucine which is an amino acid essential for human and other animals and is principally useful as a material for various drugs represented by a medicine for promoting nutrition (nutrient), and an L-isoleucine-producing bacterium belonging to the genus Escherichia, which is used in the preparation method.

Isoleucine includes two asymmetric carbon atoms and therefore, it is difficult to industrially synthesize only the L-isomer thereof by a chemical synthetic method at a low price. Moreover, there have been known methods for preparing L-isoleucine which make use of biotransformation of precursors for biosynthesis of L-isoleucine such as α-aminobutyric acid and α-ketobutyric acid. However, these methods require the use of expensive raw materials and accordingly, are not useful methods for industrially preparing L-isoleucine at a low price.

The following have been known as methods for preparing L-isoleucine through direct fermentation using cheap carbon sources and nitrogen sources: 1) methods which employ, as L-isoleucine-producing strains, mutants belonging to the genus Corynebacterium, Serratia or Escherichia resistant to the antagonists against L-isoleucine (see, for instance, Japanese Examined Patent Publication (hereunder referred to as "J. P. KOKOKU") Nos. Sho 51-21077, Sho 52-4629, Sho 56-29998 and Sho 56-3035); and 2) methods which use, as L-isoleucine-producing strains, microorganisms belonging to the genus Escherichia or Corynebacterium, in which the function of threonine deaminase or acetohydroxylic acid synthase as a key enzyme for biosynthesis of L-isoleucine is enhanced by the recombinant DNA technology (see, for instance, Japanese Un-Examined Patent Publication (hereunder referred to as "J.P. KOKAI") Nos. Hei 2-458 and Hei 2-42988).

SUMMARY OF THE INVENTION

Accordingly, it is an object of the present invention to provide a method for preparing L-isoleucine through fermentation in a high yield and at a low price.

Another object of the present invention is to provide a strain belonging to the genus Escherichia capable of effectively producing L-isoleucine.

The inventors of this invention have conducted various studies to develop a novel method for selectively preparing L-isoleucine in a high yield, have found out that the foregoing object can effectively be accomplished by the use of a specific strain belonging to the genus Escherichia and thus have completed the present invention.

According to an aspect of the present invention, there is provided an L-isoleucine-producing bacterium belonging to the genus Escherichia carrying thrABC operon comprising thrA gene coding for aspartokinase I-homoserine dehydrogenase I and substantially released from the inhibition by L-threonine; and ilvGMEDA operon which comprises ilvA gene coding for threonine deaminase and substantially released from the inhibition by L-isoleucine and from which the region required for the attenuation is deleted.

According to another aspect of the present invention, there is provided a method for preparing, through fermentation, L-isoleucine which comprises the steps of cultivating the L-isoleucine-producing bacteria belonging to the genus Escherichia in a culture medium and harvesting the L-isoleucine produced by the bacteria and accumulated in the culture medium.

BRIEF DESCRIPTION OF THE DRAWINGS

In FIG. 1, the abbreviation H represents the HindIII-incision site present on the DNA; P likewise represents the PstI-incision site; K represents the KpnI-incision site; B represents the BamHI-incision site; X represents the XbaI-incision site; and Sm represents the SmaI-incision site. The symbol "&" means that any further incision with a restriction enzyme is impossible.

The symbol "P→" represents a promoter; SD represents Shine-Dalgarno sequence; ATG represents the initiation codon; and TGA represents the termination codon.

The abbreviation "Ap" represents a marker gene for imparting ampicillin resistance to the transformed strain; and "Cm" represents a marker gene for imparting chloramphenicol resistance to the transformed strain.

Figure 1:
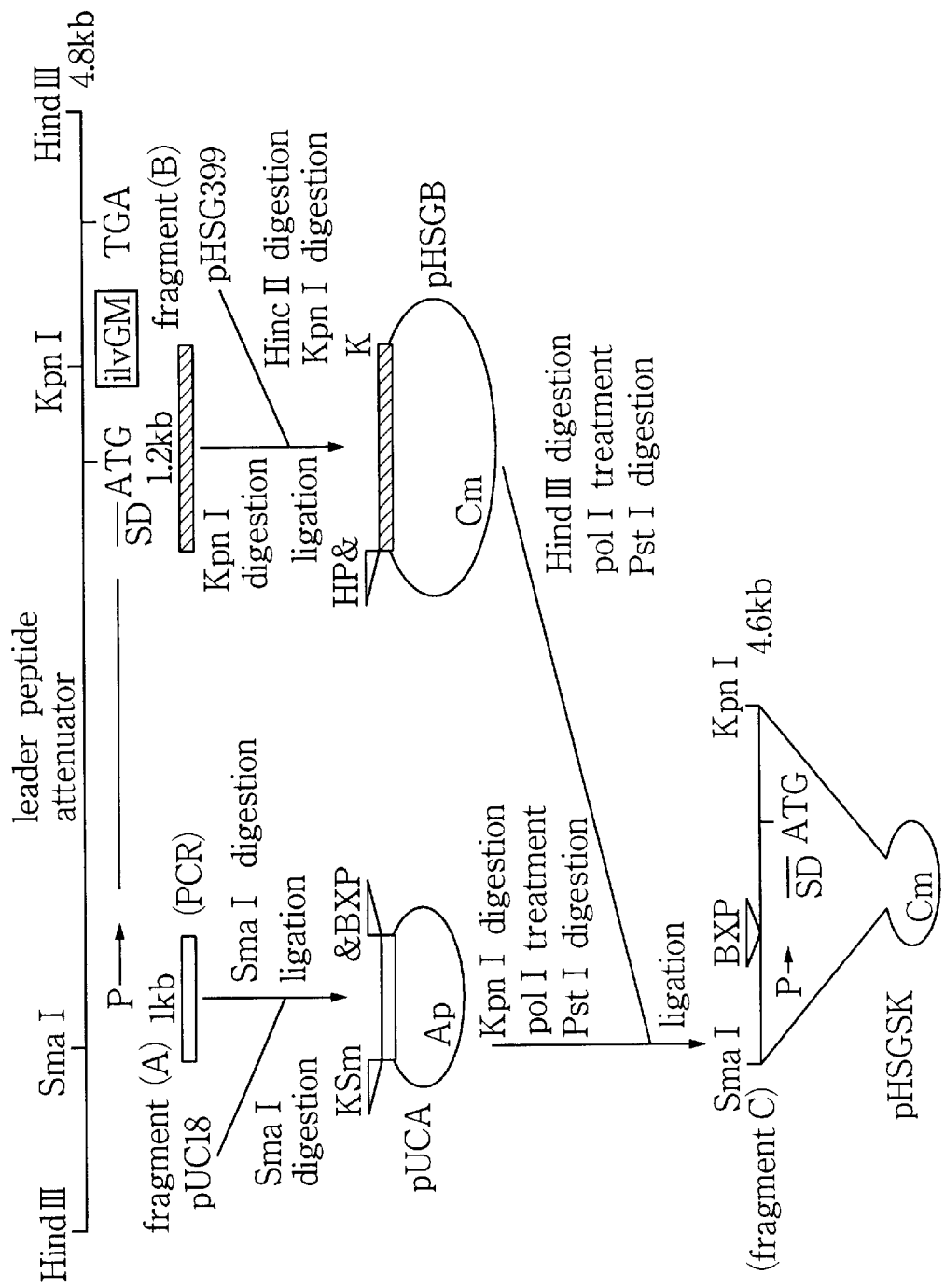
FIG. 1 is a diagram showing the procedures for constructing plasmid pHSGSK.
Figure 2:
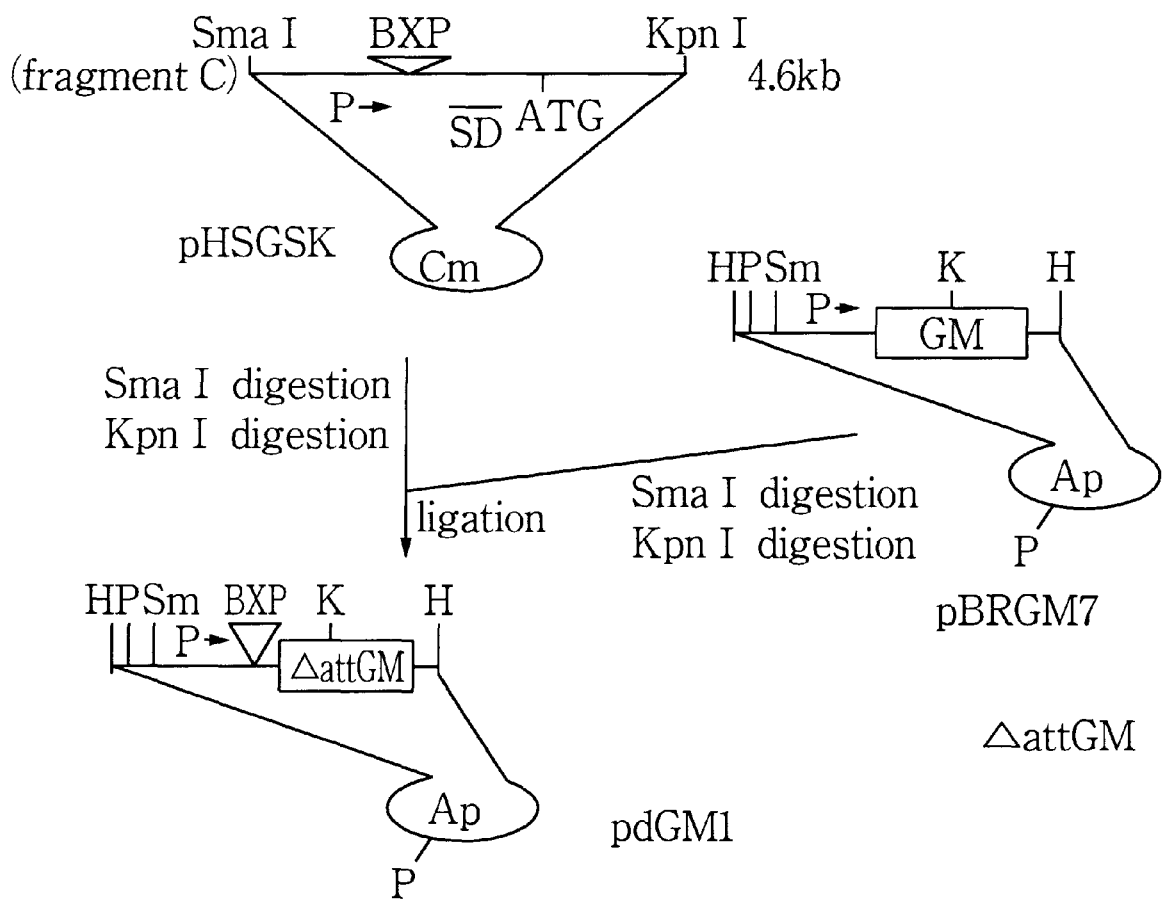

FIG. 2 is a diagram showing the procedures for preparing ilvGM gene obtained by removing the region required for the attenuation of the ilvGMEDA operon and the procedures for constructing plasmid pdGM1. The abbreviations and symbols used in FIG. 2 are the same as those used in FIG. 1.

Figure 3:
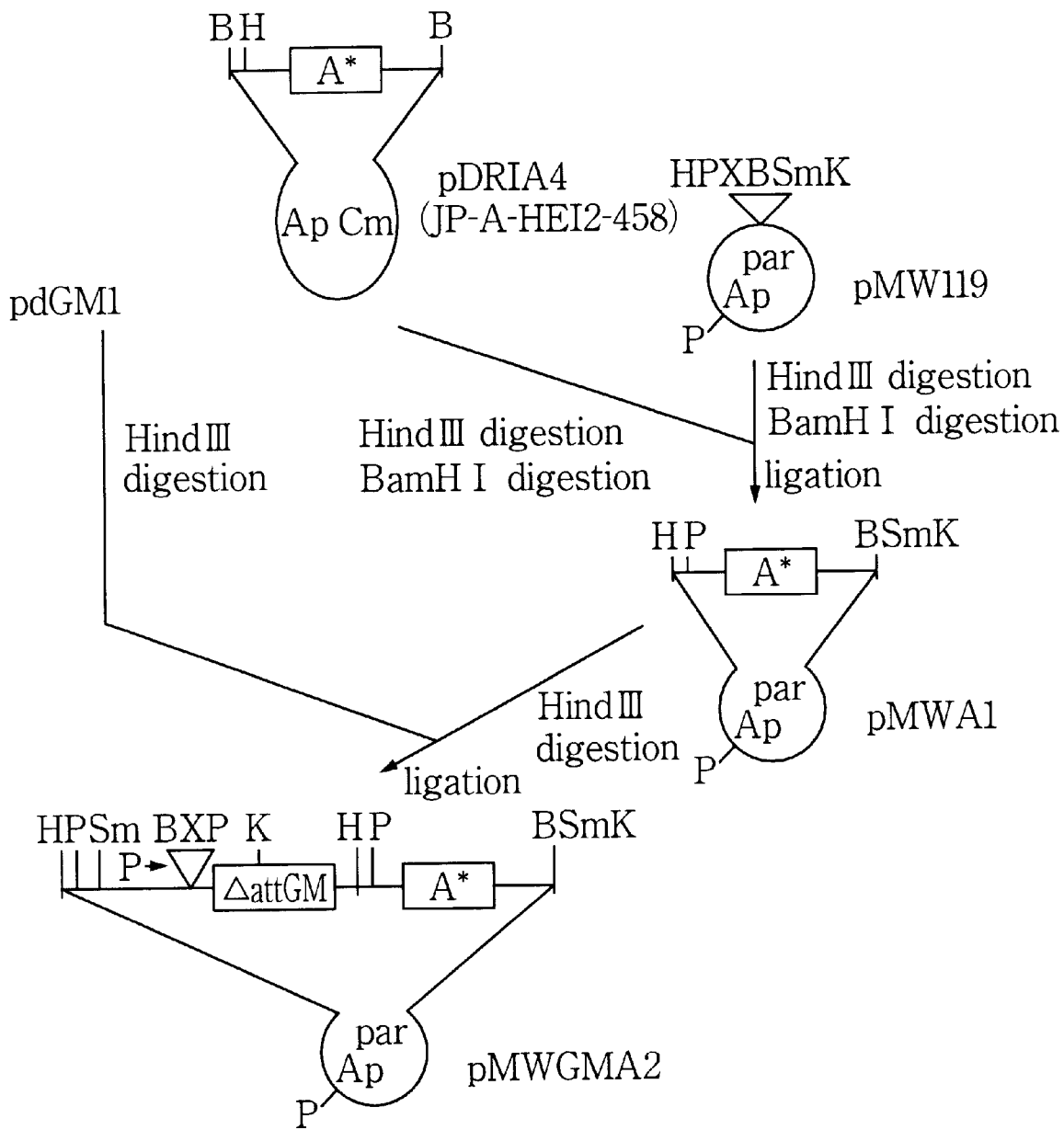

FIG. 3 is a diagram showing the procedures for constructing plasmid pMWGMA2. The abbreviations and symbols used in FIG. 3 are the same as those used in FIG. 1.

Figure 4:
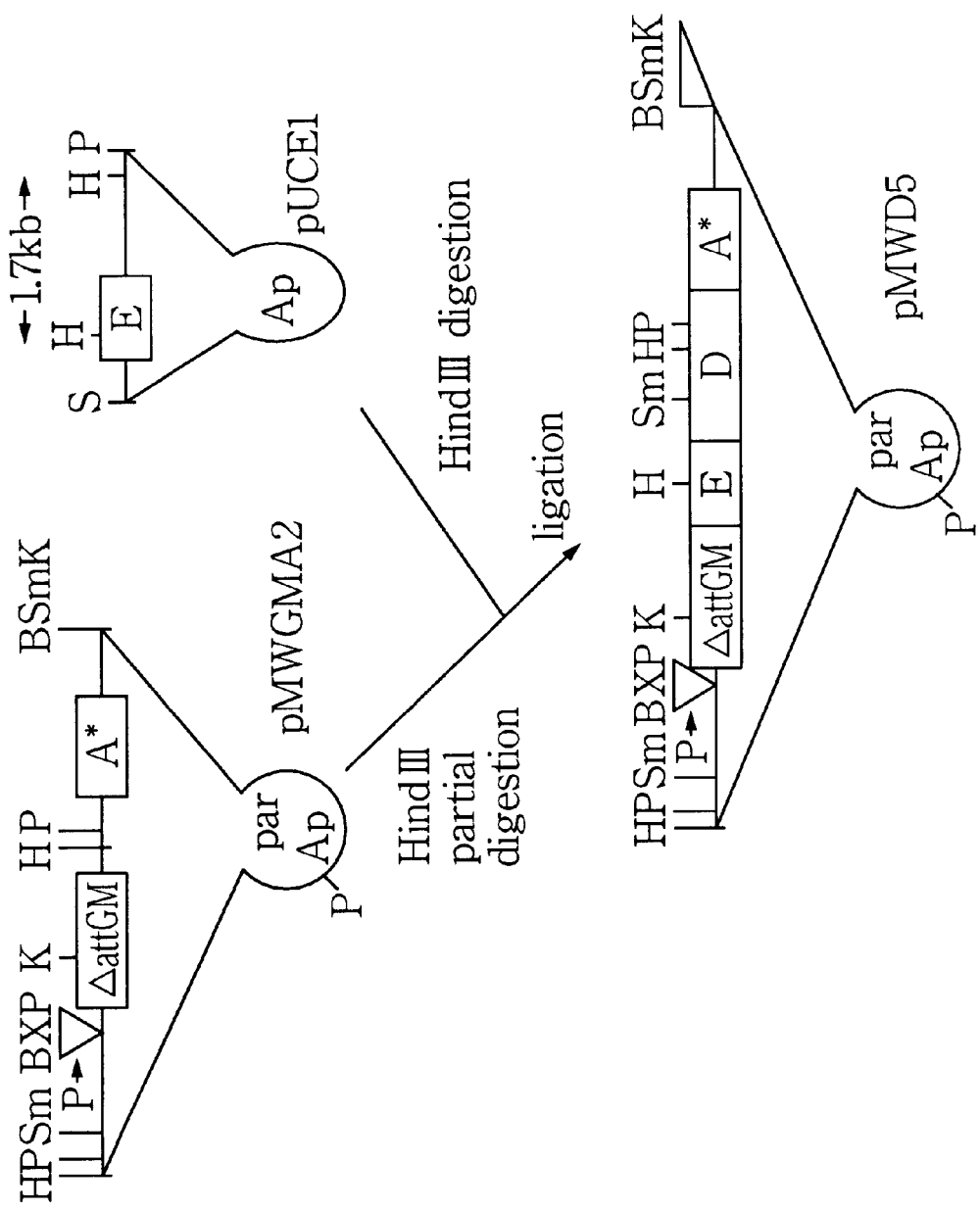

FIG. 4 is a diagram showing the procedures for constructing plasmid pMWD5. The abbreviations and symbols used in FIG. 4 are the same as those used in FIG. 1. In addition, the abbreviation "S" represents the SalI-incision site; and "par" represents the stabilized region of the plasmid.

DESCRIPTION OF THE PREFERRED EMBODIMENTS

The present invention will hereunder be explained in more detail.

The bacterium of the present invention belonging to the genus Escherichia may include a plasmid which carries the foregoing thrABC operon and ilvGMEDA operon.

The bacterium of the present invention belonging to the genus Escherichia may include two kinds of plasmids, i.e., a plasmid (A) which carries the foregoing thrABC operon and a plasmid (B) which carries the foregoing ilvGMEDA operon.

Specific examples of the ilvGMEDA operon include those comprising the DNA sequence of SEQ ID No. 1 in the Sequence Listing from which the fragment extending from 953th base to 1160th base is deleted.

Specific examples of the plasmid (A) include pVIC40 and specific examples of the plasmid (B) include pMWD5.

The foregoing bacterium belonging to the genus Escherichia is preferably *Escherichia coli*.

The bacterium belonging to the genus Escherichia according to the present invention is more preferably *Escherichia coli* carrying the thrABC operon comprising the thrA gene coding for aspartokinase I-homoserine dehydrogenase I (AKI-HDI) and substantially released from the inhibition by L-threonine; and the ilvGMEDA operon which comprises the ilvA gene coding for threonine deaminase (TD) and substantially released from the inhibition by L-isoleucine and from which the region required for the attenuation is deleted; and whose host strain is defective in thrC gene, can proliferate in the presence of 5 mg/ml of L-threonine, is defective in threonine dehydrogenase activity and has the ilvA gene possessing leaky mutation. Specific examples thereof include *Escherichia coli* AJ12919 strain.

The present invention also provides an L-isoleucine-producing bacterium belonging to the genus Escherichia carrying a thrABC operon which comprises a thrA gene coding for aspartokinase I-homoserine dehydrogenase I (AKI-HDI) and substantially released from the inhibition by L-threonine; an lysC gene coding for aspartokinase III (AKIII) and substantially released from the inhibition by L-lysine; and an ilvGMEDA operon which comprises an ilvA gene coding for threonine deaminase (TD) and substantially released from the inhibition by L-isoleucine and from which the region required for the attenuation is deleted.

The bacterium of the present invention belonging to the genus Escherichia may comprise the foregoing thrABC operon, the foregoing lysC gene and the foregoing ilvGMEDA operon in the form of a plasmid or plasmids on which they are loaded.

The bacterium of the present invention belonging to the genus Escherichia may comprise two kinds of plasmids, i.e., a plasmid (C) which carries the foregoing thrABC operon and the foregoing lysC gene and a plasmid (B) which carries the foregoing ilvGMEDA operon.

Specific examples of the ilvGMEDA operon include those comprising the DNA sequence of SEQ ID No. 1 in the Sequence Listing from which the fragment extending from 953th base to 1160th base is deleted.

Specific examples of the plasmid (C) include pVICLC*80A and specific examples of the plasmid (B) include pMWD5.

The foregoing bacterium of the present invention belonging to the genus Escherichia is preferably *Escherichia coli*.

The bacterium belonging to the genus Escherichia according to the present invention is more preferably *Escherichia coli* carrying the thrABC operon comprising the thrA gene coding for AKI-HDI and substantially released from the inhibition by L-threonine; the lysC gene coding for AKIII and substantially released from the inhibition by L-lysine; and the ilvGMEDA operon which comprises an ilvA gene coding for TD and substantially released from the inhibition by L-isoleucine and from which the region required for the attenuation is deleted; and whose host strain is defective in thrC gene, can proliferate in the presence of 5 mg/ml of L-threonine, is defective in threonine dehydrogenase activity and has ilvA gene possessing leaky mutation. Specific examples thereof include *Escherichia coli* AJ 13100 strain.

The present invention also provides a method for preparing L-isoleucine through fermentation which comprises the steps of cultivating the foregoing L-isoleucine-producing bacteria belonging to the genus Escherichia in a culture medium and harvesting the L-isoleucine produced by the bacteria and accumulated in the culture medium.

The term "thrA gene coding for aspartokinase I-homoserine dehydrogenase I and substantially released from the inhibition by L-threonine" herein used will hereunder be sometimes referred to as "released type thrA gene". In addition, the term "thrABC operon comprising thrA gene coding for aspartokinase I-homoserine dehydrogenase I and substantially released from the inhibition by L-threonine" herein used will hereunder be sometimes referred to as "released type thrABC operon".

The term "ilvA gene coding for threonine deaminase and substantially released from the inhibition by L-isoleucine" herein used will hereunder be sometimes referred to as "released type ilvA gene". In addition, the term "ilvGMEDA operon which comprises ilvA gene coding for threonine deaminase and substantially released from the inhibition by L-isoleucine (released type ilvA gene)" herein used will hereunder be sometimes referred to as "released type ilvGMEDA operon". Further the term "ilvGMEDA operon which comprises the released type ilvA gene and from which the region required for the attenuation is deleted" herein used will hereunder be sometimes referred to as "completely released type ilvGMEDA operon".

The term "aspartokinase I-homoserine dehydrogenase I" used herein will hereunder be sometimes abbreviated to "AKI-HDI" for simplicity. Moreover, the term "threonine deaminase" will sometimes be abbreviated to "TD".

In the present specification, the term "aspartokinase I-homoserine dehydrogenase I which is substantially released from the inhibition by L-threonine" will hereunder be sometimes referred to as "released type AKI-HDI". In addition, the term "threonine deaminase which is substantially released from the inhibition by L-isoleucine" will hereunder be sometimes referred to as "released type TD".

The present invention will be described below in order.

1. thrABC Operon Comprising thrA Gene Substantially Released from the Inhibition by L-Threonine The thrABC operon comprising the thrA gene coding for aspartokinase I-homoserine dehydrogenase I substantially released from the inhibition by L-threonine, i.e., the released type thrABC operon differs from wild type thrABC operon in that the thrA gene included therein suffers mutation. The mutation means one in which AKI-HDI coded by the thrA gene is released from the feedback inhibition by L-threonine.

Such a released type thrABC operon can be obtained by the following method. A DNA comprising wild type thrABC operon is first subjected to a mutagenesis treatment in vitro and then the mutagenized DNA is ligated with a vector DNA compatible with a host to give a recombinant DNA. Then the recombinant DNA is transferred into the host microorganism to give transformed microorganisms followed by selecting and separating a transformant which can express the released type AKI-HDI from the transformed microorganisms. The transformant thus isolated should carry the released type thrABC operon. Alternatively, a DNA comprising wild type thrABC operon is ligated with a vector DNA compatible with a host to give a recombinant DNA, followed by subjecting the recombinant DNA to a mutagenesis treatment in vitro, then transferring the recombinant DNA into the host microorganism to give transformed microorganisms, selecting and separating a transformant which can express the released type AKI-HDI from the transformed microorganisms. The transformant thus isolated should likewise carry the released type thrABC operon.

It is also possible to establish a released type AKI-HDI-producing mutant strain by subjecting a wild type AKI-HDI-producing microorganism to a mutagenesis treatment to thus collect the released type thrABC operon from the resulting mutant strain. Alternatively, it is likewise possible to subjecting, to a mutagenesis treatment, a transformant in which a recombinant DNA ligated with wild type thrABC operon is transferred to establish a mutagenized type AKI-HDI-producing mutant strain and then recover a recombinant DNA from the mutant strain. Thus, the released type thrABC operon may sometimes be incorporated into the resulting recombinant DNA.

As agents for mutagenizing DNA in vitro, there may be used, for instance, hydroxylamine. Hydroxylamine is a chemical mutagenic agent which causes mutation from cytosine to thymine through convesion of cytosine into N4-hydroxycytosine. On the other hand, if a microorganism per se is subjected to mutagenesis, the mutation thereof is performed by irradiation with ultraviolet rays or through the use of a mutagenic agent commonly used in the artificial induction of mutation such as N-methyl-N'-nitro-N-nitrosoguanidine (NTG).

The thrABC operon usable herein may be those derived from bacteria belonging to the genus Escherichia, in particular, the thrABC operon originated from *Escherichia coli* (hereunder also referred to as "*E. coli*").

If the thrABC operon originated from the bacteria belonging to the genus Escherichia is used, any microorganisms belonging to the genus Escherichia may be used as bacteria which serve as donors of DNA's comprising wild type thrABC operons. Specific examples thereof are those listed in "Neidhardt, F. C. et al., *Escherichia coli* and *Salmonella typhimurium*, American Society for Microbiology, Washington D.C., 1208, Table 1". More specifically, *E. coli* JM109 strain and MC1061 strain may be used in the present invention. If a wild type strain is used as the bacterium serving as a donor of the DNA comprising wild type thrABC operon, the DNA comprising wild type thrABC operon can be obtained.

(1) Preparation of Wild Type thrABC Operon

An example of the method for preparing a DNA comprising thrABC operon will now be described below. First of all, an *E. coli* strain carrying wild type AKI-HDI such as MC1061 strain is cultivated to give a culture medium. The foregoing microorganism can be cultured according to the usual solid culture method, but preferably by the liquid culture method from the viewpoint of the efficiency for collecting the bacterial cells. The medium usable herein may be, for instance, yeast extract, peptone, trypton or meat extract, supplemented with sodium chloride (NaCl). One specific example thereof is L-broth (comprising 1% bactotrypton, 0.5% bactoyeast extract, 0.5% NaCl, 0.1% glucose, pH=7.2). In this respect, the initial pH value of the medium is preferably adjusted to 6 to 8. The cultivation of the microorganism is carried out at a temperature ranging from 30 to 42° C., preferably about 37° C. for 4 to 24 hours according to, for instance, aeration-agitation submerged culture, shaking culture or static culture.

The culture medium thus obtained is then centrifuged at, for instance, 3,000 rpm for 5 minutes to recover bacterial cells of the *E. coli* MC1061 strain. The chromosomal DNA can be isolated from the resulting bacterial cells by, for instance, the method disclosed in SAITO & MIURA, Biochem. Biophys. Acta., 1963, 72, p. 619 or K. S. Kirby, Biochem. J., 1956, 64, p. 405.

The chromosomal DNA library is made up for the isolation of the thrABC operon from the chromosomal DNA thus obtained. To this end, the chromosomal DNA is partially digested by an appropriate restriction enzyme to give a mixture of various DNA fragments. For instance, the chromosomal DNA is treated with Sau3AI at a temperature of not less than 30° C., preferably 37° C., for various times ranging from one minute to 2 hours at an enzyme concentration ranging from 1 to 10 Unit/ml to thus digest the chromosomal DNA.

Then the chromosomal DNA fragment thus cleaved through the digestion is ligated with a vector DNA capable of undergoing automonous replication in a bacterial cell belonging to the genus Escherichia to give a recombinant DNA. More specifically, the vector DNA is completely digested by acting, on a vector DNA, a restriction enzyme such as BamHI which can generate a terminal base sequence identical to that of the restriction enzyme Sau3AI used for the cleavage of the chromosomal DNA thereon at a temperature of not less than 30° C. for not less than one hour, preferably 1 to 3 hours at an enzyme concentration ranging from 1 to 100 Unit/ml to thus cut and cleave the vector DNA. Then the mixture of the chromosomal DNA fragments thus prepared is admixed with the cut and cleaved vector DNA followed by acting a DNA ligase, preferably T4DNA ligase on the mixture at a temperature ranging from 4 to 16° C. for not less than one hour, preferably 6 to 24 hours at an enzyme concentration ranging from 1 to 100 Unit/ml to thus give a recombinant DNA.

A microorganism belonging to the genus Escherichia, which is a mutant defective in aspartokinase activity, such as *Escherichia coli* K-12 strain or *E. coli* Gif106M1 strain (thrA1101, metLM1000, lysC1001, ilvA, argH) is transformed with the resulting recombinant DNA to make up a chromosomal DNA library. The transformation may be carried out by, for instance, the method of D. M. Morrison (Methods in Enzymology, 1979, 68, p. 326) or a method which comprises treating a recipient cell with calcium chloride as disclosed in Mandel, M. and Higa, A., J. Mol. Biol., 1970, 53, p. 159. In this regard, the *E. coli* Gif106M1 strain is available from *E. coli* Genetic Stock Center (Connecticut, U.S.A.).

A strain whose aspartokinase activity is increased or a strain which is made up for the auxotropy due to the deletion of the gene coding for aspartokinase is selected or isolated, from the resulting chromosomal DNA library, to give a strain carrying the recombinant DNA which comprises the thrA gene.

At this stage, it is necessary to confirm whether, or not, the candidate strain carrying the thrA gene-carrying recombinant DNA carries the recombinant DNA whose thrA gene is cloned. This can be confirmed by preparing a cell extract from the candidate strain, then preparing a crude enzyme solution from the extract to examine the aspartokinase activity thereof or determine whether the activity is increased or not. The enzymatic activity of the resulting aspartokinase can be determined by the method of Stadtman et al. (Stadtman, E. R., Cohen, G. N., LeBras, G. and Robichon-Szulmajster, H., J. Biol. Chem., 1961, 236, p. 2033).

Moreover, the mutant defective in aspartokinase activity requires L-lysine, L-threonine, L-methionine and diaminopimelic acid as nutrients and therefore, if the mutant defective in aspartokinase activity is used as a host cell, the DNA fragment comprising the thrA gene can be obtained by isolating strains capable of growing on a minimal medium free of L-lysine, L-threonine, L-methionine and diaminopimelic acid or a medium free of homoserine and diaminopimelic acid and then recovering the recombinant DNA from the strain.

Incidentally, three kinds of aspartokinases are present in *E. coli* and correspondingly, there are present three kinds of genes coding for these aspartokinases therein. To confirm, under such circumstances, whether the intended thrA gene is isolated or not, it is preferred to analyze and confirm the base sequence or the restriction enzyme-cleavage pattern. In this respect, the base sequence of the thrA gene originated from *E. coli* has already been clarified and reported (Katinka, M. etal., Proc. Natl. Acad. Sci. U.S.A., 1980, 77, p. 5730).

The recombinant DNA obtained by inserting the thrA gene-containing DNA into the vector DNA can be isolated from the foregoing strain by, for instance, the method of P. Guerry etal. (J. Bacteriol., 1973, 116, p. 1064) or the method of D. B. Clewell (J. Bacteriol., 1972, 110, p. 667).

To isolate the whole length of the thrABC operon, it is necessary to freshly select the transformant carrying the whole length of the thrABC operon out of the chromosomal DNA library. More specifically, such a transformant is selected by the colony hybridization method while using the thrA gene as a probe. The colony hybridization can be performed by the usual method (Molecular Cloning, 2nd edition, Cold Spring Harbor Press (1989)).

To confirm if the whole length of the thrABC operon is isolated, the candidate DNA thus isolated is transferred into a strain which is defective in thrB gene to thus confirm the fact that the defective thrB gene is regenerated and further the isolated candidate DNA is transferred into a strain defective in thrC gene to thus confirm if the defective thrC gene is regenerated. Examples of the strains defective in the thrB gene include *E. coli* YA73 strain (thrB1000, thi-1, relA1,λ-, spoT1) and those of the strains defective in the thrC gene include *E. coli* Gif41 strain (thrC1001, thi-1, relA1, λ-, spoT1). In this connection, the *E. coli* YA73 strain and the *E. coli* Gif41 strain are available from *E. coli* Genetic Stock Center (Connecticut, U.S.A.).

Alternatively the confirmation of the fact that the whole length of the thrABC operon is isolated can be performed by a method which comprises analyzing the base sequence or restriction enzyme-cleavage pattern of the isolated candidate DNA. Incidentally, the base sequence of the *E. coli* thrB gene has already been determined and reported in Cossart, P. et al., Nucleic Acids Res., 1981, 9, p. 339. Moreover, that of the *E. coli* thrC gene has also been determined and reported in Parsot, C. et al., Nucleic Acids Res., 1983,11, p. 7331.

Wild type thrABC operon may also be prepared by isolating a chromosomal DNA from a strain carrying the wild type thrABC operon on the chromosome thereof by, for instance, the method of SAITO & MIURA and then amplifying the thrABC operon by the polymerase chain reaction (PCR) method (White, T. J. et al., Trends Genet., 1989, 5, p. 185). The DNA primers used in the amplification reaction are those complementary to both 3'-terminals of double-stranded DNA comprising a part or the whole region of the thrABC operon. If only a part of the thrABC operon is amplified, it is necessary to subject the chromosomal DNA library to screening using the isolated DNA fragment as a probe to thus select a DNA fragment comprising the whole region of the operon. On the other hand, if the whole region of the thrABC operon is amplified, the PCR reaction solution containing the DNA fragment which carries the amplified thrABC operon is subjected to the agarose gel electrophoresis and then the intended DNA fragment is extracted to thus recover the DNA fragment comprising the thrABC operon.

The DNA primer used in the amplification reaction may appropriately be prepared on the basis of, for instance, the sequence which is known in *E. coli*. The base sequence of the thrA gene originated from *E. coli* is disclosed in Katinka, M. et al., Proc. Natl. Acad. Sci. U.S.A., 1980, 77, P. 5730, that of the thrb gene of *E. coli* in Cossart, P. et al., Nucleic Acids Res., 1981, 9, p. 339 and that of the thrC gene of *E. coli* in Parsot, C. et al., Nucleic Acids Res., 1983, 11, p. 7331.

The primer DNA can be synthesized using a commercially available synthesizer (such as DNA Synthesizer Model 380B available from Applied Biosystems Company) according to the method currently used such as phosphoamidite method (Tetrahedron Letters, 1981, 22, p. 1859). In addition, the PCR method can be carried out, using a commercially available PCR reactor (such as DNA Thermal Cycler Model PJ2000 available from Parkin Elmer Company) and TaqDNA Polymerase (available from Takara Shuzo Co., Ltd.) by the method specified by the supplier.

The thrABC operon amplified by the PCR method is connected to a vector DNA capable of undergoing autonomous replication in a bacterial cell belonging to the genus Escherichia to thus transfer it into the bacterial cell. This makes the operations such as the mutagenesis of the thrA gene easy. The vector DNA used, the method for transformation and the method for confirming the presence of the thrABC operon used in the amplification are the same as those discussed above.

(2) Mutagenesis of thrABC Operon

Examples of the methods for inducing mutations such as substitution, insertion and/or deletion of amino acid residues in the thrABC operon prepared by the foregoing manner include the recombinant PCR method (Higuchi, R., 61, PCR Technology (Erlich, H. A. Eds., Stockton Press (1989)) and the partial specific mutagenesis (Kramer, W. and Frits, H. J., Meth. in Enzymol., 1987, 154, p. 350; Kunkel, T. A. et al., Meth. in Enzymol., 1987, 154, p. 367). The use of these methods permit the induction of any intended mutation at predetermined sites.

Alternatively, the chemical synthesis of an intended gene also permits induction of any mutation at predetermined sites or induction of random mutations.

Moreover, the induction of mutations may be carried out by a method comprising directly treating the thrABC operon on a chromosome or a plasmid with hydroxylamine (Hashimoto, T. and Sekiguchi, M., J. Bacteriol., 1984, 159, p. 1039). In addition, mutations may be induced by irradiating a bacterium belonging to the genus Escherichia carrying the thrABC operon with ultraviolet rays or by treating the bacterium with a chemical agent such as N-methyl-N'-nitro-N-nitrosoguanidine or nitrous acid. These methods permit the induction of random mutations.

A method for selecting the released type thrABC operon comprises first directly inducing mutation by treating the recombinant DNA comprising a DNA fragment containing the thrABC operon and a vector DNA with, for instance, hydroxylamine to give a mutant DNA and transforming, for instance, *E. coli* Gif106M1 strain with the DNA to give a transformant. Then the transformed strain is cultured in a minimal medium such as M9 containing an antagonist against L-threonine such as α-amino-β-hydroxyvaleric acid (AHV). The strain carrying the recombinant DNA comprising the wild type thrABC operon is limited in the synthesis of L-homoserine and diaminopimelic acid (DAP) and thus the growth thereof is suppressed since AKI-HDI expressed by the recombinant DNA is inhibited by AHV. Contrary to this, The strain carrying the recombinant DNA comprising the thrABC operon which comprises the thrA gene coding for AKI-HDI substantially released from the inhibition by L-threonine should grow in the minimal medium supplemented with AHV since the released type AKI-HDI coded by the thrA gene present in the recombinant DNA is not inhibited by AHV. Thus, the strain carrying the recombinant DNA comprising the thrABC operon which contains the released type thrA gene released from the inhibition, i.e., the strain resistant to AHV can be selected while making use of this phenomenon.

A microorganism which carries AKI-HDI released from the feedback inhibition and is improved in the expression of enzymes involved in the L-threonine synthesis system coded by the thrABC operon can be established by incorporating the released type thrABC operon thus obtained into an appropriate host microorganism as the recombinant DNA to thus express the recombinant DNA in the host. The host used herein is preferably microorganisms belonging to the genus Escherichia such as *Escherichia coli* (*E. coli*).

Alternatively, it is also possible to use a product obtained by isolating the released type thrABC operon from the recombinant DNA and then inserting it into a vector DNA other than that used above. The vector DNA used in the present invention is preferably plasmid vector DNA such as pUC19, pUC18, pBR322, pHSG299, pHSG298, pHSG399, pHSG398, RSF1010, pMW119, pMW118, pMW219 and pMW218. In addition, vectors of phage DNA may also be used in the present invention.

Furthermore, the transcription control region (operator or attenuator) positioned upstream of the released type thrABC operon may be removed to ensure the effective expression of the released type thrABC operon. Moreover, other promoters, such as lac, trp and PL, which can act within the microorganism may be ligated or the promoter peculiar to the thrABC operon may be amplified.

The released type thrABC operon may be included in a host in the form of a non-chromosomal DNA such as a plasmid by incorporating the product obtained by inserting the thrABC operon into a vector DNA having an ability of undergoing automonous replication, as has been discussed above. Alternatively, the thrABC operon may be incorporated into the chromosome of a host microorganism by a method which makes use of transduction, transposon (Berg, D. E. and Berg, C. M., Bio/Technol., 1983, 1, p. 417), Mu phage (J.P. KOKAI No. Hei 2-109985) or homologous recombination (Experiments in Molecular Genetics, Cold Spring Harbor Lab., 1972).

2. ilvGMEDA Operon comprising ilvA Gene Substantially Released from Inhibition by L-isoleucine and from which the Region Required for Attenuation is Removed The ilvGMEDA operon comprising the ilvA gene coding for threonine deaminase substantially released from the inhibition by L-isoleucine, i.e., the released type ilvGMEDA operon differs from the wild type ilvGMEDA operon in that the ilvA gene included in the released type one includes mutations. The mutation herein means one in which TD coded by the ilvA gene is released from the feedback inhibition by L-isoleucine.

The ilvGMEDA operon which comprises the ilvA gene coding for threonine deaminase substantially released from the inhibition by L-isoleucine and from which the region required for attenuation is removed, i.e., the completely released type ilvGMEDA operon differs from the wild type ilvGMEDA operon or the released type ilvGMEDA operon in that a mutation is induced in such a manner that any attenuation does not occur, in addition to the conditions required for the released type ilvGMEDA operon. The mutation herein includes not only a mutation in which a part or the whole of the attenuator positioned 5'-upstream region of the ilvGMEDA operon, but also a mutation in which a novel DNA fragment is inserted into the attenuator.

The released type ilvGMEDA operon is obtained by the following method. First, a DNA comprising the wild type ilvGMEDA operon is subjected to a mutagenesis treatment in vitro and the resulting mutagenized DNA is ligated to a vector DNA compatible with a host to construct a recombinant DNA. The recombinant DNA is then incorporated into the host microorganism to obtain transformants, followed by selecting, from the resulting transformants, a transformant which can express the released TD. The transformant thus selected should carry the released type ilvGMEDA operon. Alternatively, the transformant which can express the released TD can also be constructed by ligating a DNA comprising the wild type ilvGMEDA operon with a vector DNA compatible with a host to give a recombinant DNA, subjecting the recombinant DNA to a mutagenesis treatment in vitro, incorporating the resulting mutagenized recombinant DNA into the host microorganism to give transformants and then selecting, from the transformants thus obtained, a transformant which can express the released TD.

The released type ilvGMEDA operon may likewise be obtained by subjecting a wild type TD-producing microorganism to mutagenesis treatment to establish a wild type TD-producing mutant strain and isolating the intended released type ilvGMEDA operon from the mutant strain. The released type ilvGMEDA operon may also be obtained by subjecting a transformant in which a recombinant DNA is ligated with the wild type ilvGMEDA operon to a mutagenesis treatment to construct a mutant strain capable of producing the mutagenized type TD and then recovering the recombinant DNA from the mutant strain. Thus, the released type ilvGMEDA operon can sometimes formed on the recombinant DNA.

As agents for in vitro mutagenesis of DNA's, there may be used, for instance, hydroxylamine. Hydroxylamine is a chemical mutagenic agent which can induce mutation from cytosine to thymine through convesion of cytosine into N4-hydroxycytosine. On the other hand, if a microorganism per se is subjected to a mutagenesis treatment, the mutation thereof is performed by irradiation with ultraviolet rays or through the use of a mutagenic agent commonly used in the artificial mutagenesis such as N-methyl-N'-nitro-N-nitrosoguanidine (NTG).

The ilvGMEDA operon usable herein may be those derived from bacteria belonging to the genus Escherichia, in particular, the ilvGMEDA operon originated from *Escherichia coli* (*E. coli*).

If the ilvGMEDA operon originated from the bacteria belonging to the genus Escherichia is used, any microorganisms belonging to the genus Escherichia may be used as bacteria which serve as donors of DNA's comprising the wild type ilvGMEDA operons. Specific examples thereof are those listed in "Neidhardt, F. C. et al., *Escherichia coli* and *Salmonella typhimurium*, American Society for Microbiology, Washington D.C., 1208, Table 1". If a wild type strain is used as the bacterium serving as a donor of the DNA comprising the wild type ilvGMEDA operon, a DNA comprising the wild type ilvGMEDA operon can be obtained.

In this respect, if *E. coli* is used as a DNA-donor for the wild type ilvGMEDA operon, the K12 wild type strain does not express isozyme II of the active acetohydroxylic acid synthase (AHASII) since the ilvG gene thereof has a frame-shift mutation (Proc. Natl. Acad. Sci. U.S.A., 1991, 78, p. 922). For this reason, the K12 strain should be used as a DNA-donor after establishing a mutant strain whose frame is regenerated such that the activity of acetohydroxylic acid synthase II coded by the ilvG gene is regenerated. Alternatively, only the ilvG gene is isolated while using an *E. coli* strain other than those originated from the K12 strain as a DNA-donor and then incorporated into the ilvGMEDA operon derived from the K12 strain. More specifically, the ilVMEDA operon portion is isolated from the K12 strain as a DNA-donor bacterium, only the ilvG gene is separately isolated while using an *E. coli* strain other than those originated from the K12 strain as a DNA-donor, followed by ligating them to give the ilvGMEDA operon of complete length. Incidentally, the isozyme II of the acetohydroxylic acid synthase (AHASII) is composed of two large and small sub-units and the large sub-unit is coded by the ilvG gene. On the other hand, the small sub-unit is coded by the ilvM gene.

The completely released type ilvGMEDA operon can be obtained by the following method.

The position of the attenuator present in the 5'-upstream region of the ilvGMEDA operon and the base sequence thereof are reported by R. P. Lawther (Nucleic Acids Res., 1987, 15, p. 2137). The completely released type ilvGMEDA operon can be prepared through the preparation of the ilvGMEDA operon from which the attenuator is completely removed using the released type ilvGMEDA operon as a starting material.

The base sequence of SEQ ID No. 1 in the Sequence Listing discloses the region required for the attenuation. The DNA sequence extending from 999th base to 1007th base codes for the sequence comprising a series of valine residues present in the leader peptide. The DNA sequence extending from 1008th base to 1016th base codes for the sequence comprising a series of isoleucine residues present in the leader peptide (SEQ ID No: 2). On the other hand, the DNA sequence extending from 1081th base to 1104th base codes for the portion which forms a ρ-independent terminator-like stem-and-loop DNA present in the attenuator.

If L-leucine is present in a cell in a sufficient amount, the ρ-independent terminator-like stem-and-loop DNA is formed by the RNA transcribed by the DNA sequence extending from 1081th base to 1104th base, the transcription by the RNA polymerase is accordingly terminated and therefore, any ilvGMEDA operon is not expressed.

L-Isoleucine deficiency in a cell results in the lack of isoleucine-bonded tRNA in the cell and this in turn leads to interruption of the translation, by the ribosome, at the portion comprising a series of isoleucine residues present in the region which codes for the leader peptide. For this reason, mRNA forms a new conformation and as a result, there is not observed any formation of the ρ-independent terminator-like stem-and-loop which has been formed by the RNA transcripted by the DNA sequence extending from 1081th base to 1104th base. Accordingly, the transcription by the RNA polymerase is continued to thus express the ilvGMEDA operon.

Therefore, it is sufficient to remove, from the DNA sequence of SEQ ID No. 1 in the Sequence Listing, the DNA sequence extending from 1008th base to 1016th base or the DNA sequence extending from 1081th base to 1104th base, in order to remove the region required for the attenuation.

In this respect, the passage "to remove the region required for the attenuation" means the fact that the corresponding DNA or gene is mutagenized in such a manner that it does not undergo any attenuation. Therefore, the mutation is not limited to one in which all of the attenuators present in the 5'-upstream region of the ilvGMEDA operon are removed. Consequently, the mutation may be one in which the attenuator cannot form the ρ-independent terminator-like stem-and-loop. Alternatively, the gene or DNA may be mutagenized in such a manner that the leader peptide does not include the portion comprising a series of isoleucine residues. This is because the attenuation does not fulfill the desired function, in any case.

The "mutation" herein means the removal of a part or the whole of the attenuators present in the 5'-upstream region of the ilvGMEDA operon and the removal of the portions near the attenuators as well as the insertion of a new DNA fragment into the attenuators.

Moreover, the ilvGMEDA operon which carries the ilvA gene coding for threonine deaminase substantially released from the inhibition by L-isoleucine and whose region required for the attenuation is removed, i.e., the completely released type ilvGMEDA operon can also be prepared by inducing a mutation in wild type ilvGMEDA operon to thus inhibit the attenuation and then inducing a mutation in the ilvA gene included in the ilvGMEDA operon in such a manner that the expression of threonine deaminase coded by the ilvA gene is substantially released from the inhibition by L-isoleucine.

(1) Preparation of Wild Type ilvGMEDA Operon

The DNA comprising the ilvGMEDA Operon may be prepared by a method comprising the steps of separately preparing ilvGM, ilvE, ilvD and ilvA genes and then ligating these genes.

First of all, an *E. coli* strain carrying wild type TD such as *E. coli* K12 strain, *E. coli* W3110 strain, *E. coli* MC1061 strain (these three strains have undergone frame-shift); or *E. coli* MI162 strain (thr-10, car-94, λ-, relA1, ilvG603, thi-1) or *E. coli* B strain (these two strains carry normal ilvG gene) is cultivated to give a culture medium. The foregoing microorganism can be cultured according to the usual solid culture method, but preferably by the liquid culture method from the viewpoint of the efficiency for collecting the bacterial cells. The medium usable herein may be, for instance, yeast extract, peptone, trypton or meat extract, supplemented with sodium chloride (NaCl). One specific example thereof is L-broth (comprising 1% bactotrypton, 0.5% bactoyeast extract, 0.5% NaCl, 0.1% glucose, pH=7.2). In this respect, the initial pH value of the medium is preferably adjusted to 6 to 8. The cultivation of the microorganism is carried out at a temperature ranging from 30 to 42° C., preferably about 37° C. for 4 to 24 hours according to, for instance, aeration-agitation submerged culture, shaking culture or static culture. In this respect, *E. coli* MI162 strain is available from *E. coli* Genetic Stock Center (Connecticut, U.S.A.). The index number of the strain is CGSC5919. Detailed characteristic properties thereof are disclosed in Mol. Gen. Genet., 1976, 143, p. 243; J. Bacteriol., 1982, 149, p. 294.

The culture medium thus obtained is then centrifuged at, for instance, 3,000 rpm for 5 minutes to recover the bacterial cells of the *E. coli* strain. The chromosomal DNA can be isolated from the resulting bacterial cells by, for instance, the method disclosed in SAITO & MIURA, Biochem. Biophys. Acta., 1963, 72, p. 619 or K. S. Kirby, Biochem. J., 1956, 64, p. 405.

The chromosomal DNA library is made up for the isolation of ilvGMEDA operon from the chromosomal DNA thus obtained. To this end, the chromosomal DNA is partially digested by an appropriate restriction enzyme to give a mixture of various DNA fragments. For instance, the chromosomal DNA is treated with Sau3AI at a temperature of not less than 30° C., referably 37° C., for various times ranging from one minute to 2 hours at an enzyme concentration ranging from 1 to 10 Unit/ml to thus digest the chromosomal DNA.

Then the chromosomal DNA fragment thus cleaved through the digestion is ligated with a vector DNA capable of undergoing automonous replication in a bacterial cell belonging to the genus Escherichia to give a recombinant DNA. More specifically, the vector DNA is completely digested by acting a restriction enzyme such as BamHI which can generate a terminal base sequence identical to that formed by the restriction enzyme Sau3AI used for the cleavage of the chromosomal DNA thereon at a temperature of not less than 30° C. for not less than one hour, preferably 1 to 3 hours at an enzyme concentration ranging from 1 to 100 Unit/ml to thus cut and cleave the vector DNA. Then the mixture of the chromosomal DNA fragments thus prepared is admixed with the cut and cleaved vector DNA followed by acting a DNA ligase, preferably T4DNA ligase on the mixture at a temperature ranging from 4 to 16° C. for not less than one hour, preferably 6 to 24 hours at an enzyme concentration ranging from 1 to 100 Unit/ml to thus give a recombinant DNA.

Then a chromosomal DNA library is established by transforming, with the resulting recombinant DNA, a microorganism belonging to the genus Escherichia, for instance, a mutant strain thereof defective in acetohydroxylic acid synthase such as *E. coli* MI262 strain (leuB6, ilvI614, ilvH612, λ-, relA1, spoT1, ilvB619, ilvG603, ilvG605 (am), thi-1); a mutant strain thereof defective in transaminase B such as *E. coli* AB2070 strain (proA2, trp-3, hisG4, ilvE12, metE46, thi-1, ara-9, lacY1 or lacZ4, galK2, malA1, mtl-1, rpsL8 or rpsL9, ton-1, sx-3, λR, λ-, supE44); a mutant strain thereof defective in dihydroxylic acid dehydratase such as *E. coli* AB1280 strain (hisG1, ilvD16, metB1, argH1, thi-1, ara-13, lacY1 or lacZ4, gal-6, xyl-7, mtl-2, malA1, rpsL8, 9 or 17, tonA2, λR, λ-, supE44); or a mutant strain thereof defective in threonine deaminase such as *E. coli* AB1255 strain (thi-1, ilvA201, argH1, metB1, higG1, lacY1 or lacZ4, malA1, mtl-2, xyl-7, ara-13, gal-6, rpsL8, 9 or 17, tonA2, tsx-5, λR, λ-, supE44). The transformation may be carried out by, for instance, the method of D. M. Morrison et al. (Methods in Enzymology, 1979, 68, p. 326) or the method of Mandel, M. et al. (Mandel, M. & Higa, A., J. Mol. Biol., 1970, 53, p. 159) which comprises the step of treating recipient bacterial cell with calcium chloride to improve the permeability of the DNA. In this connection, the *E. coli* MI262 strain is available from *E. coli* Genetic Stock Center (Connecticut, U.S.A.). The index number thereof is CGSC5769. The detailed characteristic properties thereof are disclosed in Mol. Gen. Genet., 1977, 156, p. 1. On the other hand, the *E. coli* AB2070 strain is also available from *E. coli* Genetic Stock Center (Connecticut, U.S.A.). The index number thereof is CGSC2070. The detailed characteristic properties thereof are disclosed in J. Bacteriol., 1972, 109, p. 730. In addition, *E. coli* AB1280 strain is likewise available from *E. coli* Genetic Stock Center (Connecticut, U.S.A.). The index number thereof is CGSC1280. Moreover, *E. coli* AB1255 strain is available from *E. coli* Genetic Stock Center (Connecticut, U.S.A.). The index number thereof is CGSC1255. The detailed characteristic properties thereof are disclosed in J. Bacteriol., 1972, 109, p. 730.

Incidentally, since the base sequence of the ilvGMEDA operon is completely revealed (Nucleic Acids Res., 1987,15, p. 2137), a DNA fragment carrying a desired gene and having a predetermined length can be obtained by digesting the chromosomal DNA with a properly selected particular restriction enzyme. More preferably, an intended DNA fragment carrying a desired gene can more efficiently be prepared by ligating only the DNA fragment having a predetermined length with a vector DNA to give a recombinant DNA and then preparing the chromosomal DNA library using the resulting recombinant DNA.

A strain whose acetohydroxylic acid synthase activity is increased or a strain which is made up for the auxotropy due to the deletion of the gene coding for acetohydroxylic acid synthase is selected or isolated, from the resulting chromosomal DNA library, to give a strain carrying the recombinant DNA which comprises the ilvGM gene.

Moreover, a strain whose transaminase B activity is increased or a strain which is made up for the auxotropy due to the deletion of the gene coding for transaminase B is selected or isolated, from the resulting chromosomal DNA library, to give a strain carrying the recombinant DNA which comprises the ilvE gene.

Further, a strain whose dihydroxylic acid dehydratase activity is increased or a strain which is made up for the auxotropy due to the deletion of the gene coding for dihydroxylic acid dehydratase is selected or isolated, from the resulting chromosomal DNA library, to give a strain carrying the recombinant DNA which comprises the ilvD gene.

In addition, a strain whose threonine deaminase activity is increased or a strain which is made up for the auxotropy due to the deletion of the gene coding for threonine deaminase is selected or isolated, from the resulting chromosomal DNA library, to give a strain carrying the recombinant DNA which comprises the ilvA gene.

At this stage, it is necessary to confirm whether, or not, the candidate strain carrying the recombinant DNA, which comprises the ilvGM gene, carries the recombinant DNA whose ilvGM gene is cloned. This can be confirmed by preparing a cell extract from the candidate strain, then preparing a crude enzyme solution from the extract to examine whether the acetohydroxylic acid synthase activity thereof is increased or not. The enzymatic activity of the acetohydroxylic acid synthase can be determined by the method of M. D. Felice et al. (Methods in Enzymology, 166, p. 241).

Moreover, the mutant strain defective in acetohydroxylic acid synthase activity requires isoleucine, leucine and valine and therefore, if the mutant strain defective in acetohydroxylic acid synthase activity is used as a host cell, a DNA fragment comprising the ilvGM gene can be obtained by isolating strains capable of growing on a minimal medium free of valine and then recovering the recombinant DNA from the strain.

Moreover, the base sequence of the DNA comprising the ilvGM gene has been reported by R. P. Lawther et al. (Nucleic Acids Res., 1987, 15, p. 2137). For this reason, the confirmation may likewise be performed by isolating the recombinant DNA from the candidate strain, then determining the base sequence thereof and comparing the base sequence thus determined with that disclosed in the article.

The open reading frame of the ilvG gene of the *E. coli* K12 strain include a mutation as has been discussed above. As a result, a frame shift consequently takes place and the transcription is terminated because of the appearance of a termination codon in the middle of the frame. More specifically, the termination codon appears at the 982th to 984th position counting from the DNA sequence of the initiation codon ATG (1st to 3rd sequence). Therefore, if the ilvGM gene isolated from the strain is used, it is necessary to return the mutagenized portion to the normal one by the site-directed mutagenesis method. In case of, for instance, the ilvG gene (ilvG603) of the *Escherichia coli* MI162 strain, the frame is returned to its normal condition by inserting two pairs of bases of TG into the gene at the position before the termination codon TGA which appears therein at the 982th to 984th position. Further details thereof are disclosed in FIG. 2 of J. Bacteriol., 1982, 149, p. 294.

Moreover, it is necessary to confirm whether, or not, the candidate strain carrying the recombinant DNA, which comprises the ilvE gene, carries the recombinant DNA whose ilvE gene is cloned. Since the mutant strain defective in transaminase B activity requires isoleucine for its growth. Therefore, if the mutant strain is used as a host microorganism, a DNA fragment comprising the ilvE gene can be obtained by isolating the strain capable of growing on a minimal medium free of isoleucine and then recovering the recombinant DNA from the strain.

Alternatively, the base sequence of the DNA comprising the ilvE gene has been reported by R. P. Lawther et al. (Nucleic Acids Res., 1987, 15, p. 2137). For this reason, the confirmation may likewise be performed by isolating the recombinant DNA from the candidate strain, then determining the base sequence thereof and comparing the base sequence thus decoded with that disclosed in this article.

Further, it is necessary to confirm whether, or not, the candidate strain carrying the recombinant DNA, which comprises the ilvD gene, carries the recombinant DNA whose ilvD gene is cloned. Since the mutant strain defective in the gene coding for dihydroxylic acid dehydratase requires isoleucine, leucine and valine for its growth. Therefore, if the mutant strain is used as a host microorganism, a DNA fragment comprising the ilvD gene can be obtained by isolating the strain capable of growing on a medium free of valine and then recovering the recombinant DNA from the strain.

Alternatively, the base sequence of the DNA comprising the ilvD gene has been reported by R. P. Lawther et al. (Nucleic Acids Res., 1987, 15, p. 2137). For this reason, the confirmation may likewise be performed by isolating the recombinant DNA from the candidate strain, then determining the base sequence thereof and comparing the base sequence thus determined with that disclosed in this article.

The confirmation of whether, or not, the candidate strain carrying the recombinant DNA, which comprises the ilvA gene, carries the recombinant DNA whose ilvA gene is cloned can be carried out by preparing a cell extract from the candidate strain, then preparing a crude enzyme solution from the extract to examine whether the threonine deaminase activity thereof is increased or not. A method for determining the enzymatic activity of the threonine deaminase is disclosed in Methods in Enzymology, 1971, 17B, p. 555.

Moreover, the mutant strain defective in threonine deaminase activity requires isoleucine and therefore, if the mutant strain is used as a host cell, a DNA fragment comprising the ilvA gene can be obtained by isolating the strain capable of growing on a minimal medium free of isoleucine and then recovering the recombinant DNA from the strain.

Alternatively, the base sequence of the DNA comprising the ilvA gene has been reported by R. P. Lawther et al. (Nucleic Acids Res., 1987, 15, p. 2137). For this reason, the confirmation may likewise be performed by isolating the recombinant DNA from the candidate strain, then determining the base sequence thereof and comparing the base sequence thus determined with that disclosed in this article.

Each recombinant DNA can be isolated from the foregoing corresponding strain by, for instance, the method of P. Guerry et al. (J. Bacteriol., 1973, 116, p. 1064) or the method of D. B. Clewell (J. Bacteriol., 1972, 110, p. 667).

The DNA fragment comprising the ilvGM gene, the DNA fragment comprising the ilvE gene, the DNA fragment comprising the ilvD gene and the DNA fragment comprising the ilvA gene are ligated to isolate the ilvGMEDA operon of whole length. When ligating these genes, the entire base sequence of the ilvGMEDA operon already reported by R. P. Lawther et al. (Nucleic Acids Res., 1987, 15, p. 2137) may be used as the reference.

The wild type ilvGMEDA operon may also be prepared by isolating a chromosomal DNA from a strain carrying wild type ilvGMEDA operon on the chromosome thereof by, for instance, the method of SAITO & MIURA and then amplifying the ilvGMEDA operon by the polymerase chain reaction (PCR) method (White, T. J. et al., Trends Genet., 1989, 5, p. 185). The DNA primer used in the amplification reaction is one complementary to both 3'-terminals of double-stranded DNA comprising a part or the whole region of the ilvGMEDA operon. If only a part of the ilvGMEDA operon is amplified, it is necessary to subject the chromosomal DNA library to screening using the isolated DNA fragment as a probe to thus select a DNA fragment comprising the whole region of the operon. On the other hand, if the whole region of the ilvGMEDA operon is amplified, the PCR reaction solution containing the DNA fragment carrying the amplified ilvGMEDA operon is subjected to the agarose gel electrophoresis and then the intended DNA fragment is extracted to thus recover the DNA fragment comprising the ilvGMEDA operon.

When preparing the DNA primer, the entire base sequence of the ilvGMEDA operon of *E. coli* already reported by R. P. Lawther et al. (Nucleic Acids Res., 1987, 15, p. 2137) may be used as the reference.

The primer DNA can be synthesized using a commercially available synthesizer (such as DNA Synthesizer Model 380B available from Applied Biosystems Company) according to the method currently used such as phosphoamidite method (Tetrahedron Letters, 1981, 22, p. 1859). In addition, the PCR reaction can be carried out, using a commercially available PCR reactor (such as DNA Thermal Cycler Model PJ2000 available from Parkin Elmer Company) and TaqDNA Polymerase (available from Takara Shuzo Co., Ltd.) by the method specified by the supplier.

The ilvGMEDA operon amplified by the PCR method is linked to a vector DNA capable of autonomous replication in a bacterial cell belonging to Escherichia to thus transfer it into the bacterial cell. This makes the operations such as the mutagenesis of the ilvA gene and the removal of the region required for the attenuation easy. The vector DNA used, the method for transformation and the method for confirming the presence of the ilvGMEDA operon are the same as those discussed above.

(2) Induction of Mutations in ilvGMEDA Operon

Examples of the methods for inducing mutations such as substitution, insertion and/or deletion of amino acid residues in the ilvGMEDA operon prepared by the foregoing method include the recombinant PCR method (Higuchi, R., 61, PCR Technology (Erlich, H. A. Eds., Stockton Press (1989)) and the partial specific mutagenesis (Kramer, W. and Frits, H. J., Meth. in Enzymol., 1987, 154, p. 350; Kunkel, T. A. et al., Meth. in Enzymol., 1987, 154, p. 367). The use of these methods permit the induction of any intended mutation at predetermined sites.

Alternatively, the chemical synthesis of an intended gene also permits induction of any mutation at predetermined sites or induction of random mutations.

Moreover, the induction of mutations may be carried out by a method comprising directly treating the ilvGMEDA operon on a chromosome or a plasmid with hydroxylamine (Hashimoto, T. and Sekiguchi, M., J. Bacteriol., 1984, 159, p. 1039). In addition, mutations may be induced by irradiating a bacterium belonging to the genus Escherichia carrying the ilvGMEDA operon with ultraviolet rays or by treating the bacterium with a chemical agent such as N-methyl-N'-nitro-N-nitrosoguanidine or nitrous acid. These methods permit the induction of random mutations.

A method for selecting a DNA fragment carrying the released type ilvA operon comprises first directly inducing mutation by treating the recombinant DNA comprising a DNA fragment containing the ilvA gene and a vector DNA with, for instance, hydroxylamine to give a transformant of, for instance, *E. coli* W3110 strain. Then the transformed strain is cultured in a minimal medium such as M9 containing an antagonist against L-isoleucine such as an appropriate amount of glycyl-L-leucine. The strain carrying the recombinant DNA comprising the wild type ilvA gene is accordingly limited in the synthesis of L-isoleucine and thus the growth thereof is sometimes suppressed (it is rather preferred to use a vector of small copy number since the influence due to the gene-dosage effect can be reduced). Contrary to this, the strain carrying the recombinant DNA comprising the ilvA gene which codes for TD substantially released from the inhibition by L-isoleucine can synthesize an excess amount of L-isoleucine even in the presence of glycyl-L-leucine and should thus grow in the minimal medium supplemented with glycyl-L-leucine. Thus, the strain carrying the recombinant DNA comprising the released type ilvA gene which is released from the inhibition, i.e., the strain resistant to glycyl-L-leucine can be selected while making use of this phenomenon.

A microorganism which carries TD released from the feedback inhibition and is improved in the expression of enzymes involved in the L-isoleucine biosynthesis system coded by the ilvGMEDA operon can be established by incorporating the released type ilvGMEDA operon thus obtained and carrying the released type ilvA gene into an appropriate host microorganism as the recombinant DNA to thus express the recombinant DNA. The host used herein is preferably microorganisms belonging to the genus Escherichia such as *Escherichia coli* (*E. coli*).

Alternatively, it is also possible to use a product obtained by isolating the released type ilvGMEDA operon from the recombinant DNA and then inserting it into another vector DNA. The vector DNA used in the present invention is preferably plasmid vector DNA such as pUC19, pUC18, pBR322, pHSG299, pHSG298, pHSG399, pHSG398, RSF1010, pMW119, pMW118, pMW219 and pMW218. In addition, pharge DNA vectors may also be used in the present invention.

Furthermore, the transcription control region (operator or attenuator) positioned upstream of the released type ilvGMEDA operon may be removed to ensure the effective expression of the released type ilvGMEDA operon. Moreover, other promoters, such as lac, trp and PL, acting in the microorganism may be ligated or the promoter peculiar to the ilvGMEDA operon may be amplified.

The released type ilvGMEDA operon may be included in a host in the form of a non-chromosomal DNA such as a plasmid by incorporating the product obtained by inserting the ilvGMEDA operon into a vector DNA having an ability of undergoing automonous replication, as has been discussed above. Alternatively, the ilvGMEDA operon may be incorporated into the chromosome of a host microorganism by a method which makes use of transduction, transposon (Berg, D. E. and Berg, C. M., Bio/Technol., 1983, 1, p. 417), Mu phage (J.P. KOKAI No. Hei 2-109985) or homologous recombination (Experiments in Molecular Genetics, Cold Spring Harbor Lab., 1972).

(3) Removal of Region Required for Attenuation of ilvGMEDA Operon

Methods for removing the region required for the attenuation from the ilvGMEDA operon, i.e., to induce, in the ilvGMEDA operon, a mutation which permits the inhibition of the attenuation, include those in which a part or all of the attenuators present in the 5'-upstream region of the ilvGMEDA operon are removed, and those in which a new DNA fragment is inserted into the attenuator. In this connection, the term "attenuator" herein used means a base sequence forming a ρ-independent terminator-like stem-and-loop. For instance, it corresponds to the portion extending from the 1081th to 1104th bases of the base sequence of SEQ ID No. 1 in the Sequence Listing.

The removal of the attenuator may be carried out by preparing a DNA fragment of the ilvGMEDA operon existing upstream of the attenuator and separately preparing another DNA fragment of the operon existing downstream of the attenuator and then ligating these DNA fragments. For instance, the DNA fragment of the operon existing upstream of the attenuator can be prepared by cleaving the ilvGMEDA operon of complete length with an appropriate restriction enzyme. Alternatively, the DNA fragment existing upstream of the attenuator may be amplified by the PCR method. The primer DNA used in the PCR method may be chemically synthesized on the basis of the base sequences reported by R. P. Lawther et al. (Nucleic Acids Res., 1987,15, p. 2137) and the base sequence reported by G. Coppola et al. (Gene, 1991, 97, p. 21). Moreover, the DNA fragment existing upstream of the attenuator may be chemically synthesized.

The DNA fragment of the ilvGMEDA operon existing downstream of the attenuator can likewise be prepared by methods similar to those discussed above in connection with the DNA fragment existing upstream of the attenuator.

The completely released type ilvGMEDA operon can sometimes be prepared by preparing the ilvGMEDA operon in which a part of the attenuator or the portion near the attenuator is removed starting from the released type ilvGMEDA operon. The position and the base sequence of the attenuator have been reported by R. P. Lawther et al. (Nucleic Acids Res., 1987,15, p. 2137) and therefore, the DNA fragment to be removed is determined on the basis of the sequence disclosed in the article.

The DNA fragment to be removed is preferably a DNA fragment required for the formation of a ρ-independent terminator-like stem-and-loop by the attenuator; an appropriate DNA fragment comprising the region coding for a series of isoleucine residues positioned upstream of the stem-and-loop; or a DNA fragment comprising both of these regions. The removal of a part of the attenuator or the portion near the attenuator may be carried out by preparing a DNA fragment of the ilvGMEDA operon existing upstream of the DNA portion to be removed and separately preparing another DNA fragment of the operon existing downstream of the DNA portion to be removed and then ligating these DNA fragments. For instance, the DNA fragment of the operon existing upstream of the DNA portion to be removed can be prepared by cleaving the ilvGMEDA operon of complete length with an appropriate restriction enzyme. Alternatively, the DNA fragment existing upstream of the DNA portion to be removed may be amplified by the PCR method. The primer DNA used in the PCR method may be chemically synthesized on the basis of the base sequences reported by R. P. Lawther et al. (Nucleic Acids Res., 1987, 15, p. 2137) and the base sequence reported by G. Coppola et al. (Gene, 1991, 97, p. 21). Moreover, the DNA fraction existing upstream of the DNA portion to be removed may be chemically synthesized.

The DNA fragment of the ilvGMEDA operon existing downstream of the DNA portion to be removed can likewise be prepared by methods similar to those discussed above in connection with the DNA fragment existing upstream of the DNA portion to be removed.

The completely released type ilvGMEDA operon can sometimes be prepared by preparing the ilvGMEDA operon in which a new DNA fragment is inserted into the attenuator starting from the released type ilvGMEDA operon. The position and the base sequence of the attenuator have been reported by R. P. Lawther et al. and G. Coppola et al. and therefore, the position and the base sequence of the DNA fragment to be inserted are determined on the basis of the sequences disclosed in these article.

The DNA fragment is preferably inserted into the attenuator at the DNA fragment thereof required for the formation of a ρ-independent terminator-like stem-and-loop or at the DNA portion coding for a sequence comprising a series of isoleucine residues positioned upstream of the stem-and-loop. As a result of the insertion, the attenuator sometimes loses the ability of forming the ρ-independent terminator-like stem-and-loop. For this reason, it would be expected that the attenuator does not fulfill its function.

The new DNA fragment to be inserted into the attenuator is preferably designed in such a manner that the attenuator loses the ability of forming the ρ-independent terminator-like stem-and-loop through the insertion thereof and that any sequence comprising a series of isoleucine residues is not positioned upstream of the stem-and-loop.

The insertion of a new DNA fragment into the attenuator may be carried out by preparing a DNA fragment of the ilvGMEDA operon existing upstream of the DNA portion in which the new DNA fragment is inserted, separately preparing another DNA fragment of the operon existing downstream of the DNA portion in which the new DNA fragment is inserted, likewise separately preparing the new DNA fragment to be inserted and then ligating these DNA fragments. For instance, the DNA fragment of the ilvGMEDA operon existing upstream of the DNA portion in which the new DNA fragment is inserted can be prepared by cleaving a DNA fragment which comprises the ilvGMEDA operon of complete length with an appropriate restriction enzyme. Alternatively, the DNA fragment of the ilvGMEDA operon existing upstream of the DNA portion in which the new DNA fragment is inserted may be amplified by the PCR method. The primer DNA used in the PCR method may be chemically synthesized on the basis of the base sequences reported by R. P. Lawther et al. (Nucleic Acids Res., 1987, 15, p. 2137) and the base sequence reported by G. Coppola et al. (Gene, 1991, 97, p. 21). Moreover, the DNA fragment existing upstream of the DNA portion in which the new DNA fragment is inserted may be chemically synthesized.

The DNA fragment of the ilvGMEDA operon existing downstream of the DNA portion in which the new DNA fragment is inserted can likewise be prepared by methods similar to those discussed above in connection with the DNA fragment existing upstream of the DNA portion.

The new DNA fragment to be inserted may be chemically synthesized.

Moreover, when amplifying, by the PCR method, the DNA fragment of the ilvGMEDA operon existing upstream of the DNA portion in which the new DNA fragment is inserted and the DNA fragment of the ilvGMEDA operon existing downstream of the DNA portion in which the new DNA fragment is inserted, the new DNA fragment to be inserted may be ligated with a primer DNA. For instance, one of the strands of the new DNA fragment to be inserted is linked to the 3'-terminal side of the DNA primer used for amplifying the DNA fragment of the ilvGMEDA operon existing upstream of the DNA portion in which the new DNA fragment is inserted. The complementary strand of the new DNA fragment to be inserted is linked, in the same manner used above, to the 5'-terminal side of the DNA primer used for amplifying the DNA fragment of the ilvGMEDA operon existing downstream of the DNA portion in which the new DNA fragment is inserted. Then these two kinds of DNA fragments amplified through the use of these primers are ligated.

A microorganism which carries TD released from the feedback inhibition and is improved in the expression of enzymes involved in the L-isoleucine biosynthesis system coded by the ilvGMEDA operon because of the absence of the attenuation can be constructed by incorporating the completely released type ilvGMEDA operon thus obtained into an appropriate host microorganism as the recombinant DNA to thus express the recombinant DNA. The host used herein is preferably microorganisms belonging to the genus Escherichia such as *Escherichia coli* (*E. coli*).

Alternatively, it is also possible to use a product obtained by isolating the completely released type ilvGMEDA operon from the recombinant DNA and then inserting it into another vector DNA. The vector DNA used in the present invention is preferably plasmid vector DNA such as pUC19, pUC18, pBR322, pHSG299, pHSG298, pHSG399, pHSG398, RSF1010, pMW119, pMW118, pMW219 and pMW218. In addition, pharge DNA vectors may also be used in the present invention.

Furthermore, to ensure the effective expression of the completely released type ilvGMEDA operon, other promoters, such as lac, trp and PL, acting in the microorganism may be ligated at the position upstream of the completely released type ilvGMEDA operon or the promoter peculiar to the ilvGMEDA operon may be used after amplification thereof.

The completely released type ilvGMEDA operon may be included in a host in the form of a non-chromosomal DNA such as a plasmid by incorporating the product obtained by inserting the ilvGMEDA operon into a vector DNA having an ability of undergoing automonous replication, as has been discussed above. Alternatively, the ilvGMEDA operon may be incorporated into the chromosome of a host microorganism by a method which makes use of transduction, transposon (Berg, D. E. and Berg, C. M., Bio/Technol., 1983, 1, p. 417), Mu phage (J.P. KOKAI No. Hei 2-109985) or homologous recombination (Experiments in Molecular Genetics, Cold Spring Harbor Lab., 1972).

As the donor bacteria to supply the DNA containing the gene coding for AKIII (lysC), there may be used any microorganisms belonging to the genus Escherichia. Specifically, those mentioned in the writings of Neidhardt (Neidhardt, F. C. et al., *Escherichia coli* and *Salmonella typhimurium*, American Society for Microbiology, Washington,D.C., 1208, Table 1). Examples thereof include *E. coli* strains JM109 and MC1061.

If a wild strain is used as the donor bacteria to supply the DNA containing the gene coding for AKIII (lysC), then a DNA containing a wild type of AKIII gene may be obtained. For the introduction of a mutation into this gene in order to obtain an AKIII gene which releases the feedback inhibition due to L-lysine (lysC*), in vitro mutation of the DNA may be effected by direct treatment with hydroxylamine. Hydroxylamine is a chemical mutating agent which induces a mutation C→T by converting cytosine to N'-hydroxycytosine.

Further, a DNA containing the AKIII gene which is released from the feedback inhibition due to L-lysine may be obtained by using as a DNA donor strain a mutant which releases the feedback inhibition on AKIII activity due to L-lysine. This mutant may be obtained from cells which have been subjected to, for example, a conventional method for mutating treatment, exposure to ultraviolet rays or treatment with a mutating agent such as N-methyl-N'-nitro-N-nitrosoguanidine (NTG).

A description will now be provided regarding the preparation of a DNA containing a gene which codes for AKIII (lysC). First, *E. coli* having a wild type of lysC, for example, MC1061 strain, is cultured to obtain cultured cells. The culturing of the above mentioned microorganism may be carried out by a conventional solid culture method, but a liquid culture method is preferably used for the culturing from the view point of cell collection. Also, the culture medium may be one prepared for example, by adding one or more inorganic salts such as monopotassium phosphate ($KH_2PO_3$), dipotassium phosphate ($K_2HPO_3$), magnesium sulfate, sodium chloride, magnesium chloride, ferric chloride, ferric sulfate, or manganese sulfate, to one or more nitrogen sources such as yeast extract, peptone, meat extract, corn steep liquor or an effusion of soybean or wheat, and then further adding carbohydrates, vitamins, etc., if necessary. The initial pH of the culture medium is appropriately adjusted to 7–8. Also, the culturing is carried out at 30–42° C., and preferably about 37° C., for 4–24 hours, by submerged culture with aeration and stirring, shaking culture, standing culture, or the like. The cultured product which is obtained in this manner is subjected to centrifugal separation at, for example, 3,000 rpm for 5 minutes, to obtain cells of *E. coli* MC1061 strain.

Chromosomal DNA may be obtained from these cells by, for example, the method of Saito and Miura (Biochem. Biophys. Acta. 72, 619, 1963), the method of K. S. Kirby (Biochem. J. 64, 405, 1956), etc.

For isolating the lysC gene, the chromosomal DNA obtained by the above methods is cleaved using an appropriate restriction enzyme. Next, the gene may be linked to a vector DNA which is capable of replication in Escherichia bacteria, and the resulting recombinant DNA may be used to transform a mutant strain of Escherichia, for example, GT3, which lacks aspartokinase I, II and III (to create a gene library), and of the resulting transformants may be isolated a strain which has become capable of growing on a minimal culture medium without lysine, thus separating the recombinant DNA containing the lysC gene.

Concretely, a chromosomal DNA is subjected to digestion with a restriction enzyme, for example, Sau3AI at a temperature of 30° C. or higher, and preferably 37° C., at an enzyme concentration of 1–10 units/ml for various times (1 minute–2 hours) for complete digestion or partial digestion to obtain a mixture containing a variety of chromosomal DNA fragments. The vector DNA which is capable of replication in Escherichia bacteria is subjected to digestion with a restriction enzyme, for example, BamHI, which produces the same terminal base sequence as does the restriction enzyme Sau3A used for the cleavage of the chromosomal DNA, at a temperature of 30° C. or higher, at an enzyme concentration of 1–100 units/ml for 1 hour or more, and preferably 1–3 hours, to effect complete digestion thereof to obtain the cleaved DNA. Next, the mixture containing the DNA fragments which were derived from *E. coli* MC1061 and include the lysC gene prepared in the manner described above, is mixed with the cleaved DNA, and a DNA ligase, preferably T4 DNA ligase, is allowed to act thereon at a temperature of 4–16° C., at an enzyme concentration of 1–100 units/ml for 1 hour or more, preferably 6–24 hours, to obtain a recombinant DNA.

The vector DNA to be acted according to the present invention is preferably a plasmid vector DNA, for example, pUC19, pUC18, pBR322, pHSG299, pHSG399, RSF1010, etc. In addition, pharge DNA vectors may be used. Promoters which function in microorganisms, for example, lac, trp, PL and the like may be used for an efficient expression of the gene which is useful for the desired purpose. The term "recombinant DNA" used here includes DNA resulting from the incorporation of the above gene into chromosomes by methods which make use of transposons (Berg, D. E. and Berg, C. M., Bio/Technol., 1, 417, 1983), Mu phage (J.P. KOKAI No. Hei 2–109985) or homologous recombination (Experiments in Molecular Genetics, Cold spring Harbor Lab., 1972).

This recombinant DNA is used to transform, for example, *E. coli* K-12 strain, and preferably GT3 strain, etc., and then a strain which has recombinant DNA containing the lysC gene is obtained from the strains having an increased level of AK activity or from strains with complemented nutritional requirements. The transformation may be carried out according to the method of D. M. Morrison (Methods in Enzymology, 68, 326, 1979) or a method whereby the recipient cells are treated with calcium chloride to raise the degree of penetration of the DNA (Mandel, M. and Higa, A., J. Mol. Biol., 53, 159, 1970). Then, the recombinant DNA prepared by the insertion of DNA containing the lysC gene into the vector DNA may be isolated from the above mentioned strains by, for example, the method of P. Guerry, et al. (J. Bacteriol., 116, 1064, 1973) or the method of D. B. Clewell (J. Bacteriol., 110, 667, 1972).

It may be confirmed that the candidate strain in fact possesses the recombinant DNA having lysC, by preparing a cell extract solution, and then preparing therefrom a crude enzyme solution for confirmation of aspartokinase activity. The method of measuring the enzyme activity of aspartokinase may be according to the method of Stadtman, et al. (Stadtman, E. R., Cohen, G. N., LeBras, G., and Robichon-Szulmajster, H., J. Biol, Chem., 236, 2033, 1961).

Alternatively, the lysC gene may be obtained by amplifying the lysC gene from the chromosomal DNA obtained by the method of Saito and Miura, by the PCR (polymerase chain reaction; see White, T. J. et al., Trends Genet. 5, 185, 1989). The DNA primer to be used for he amplification is one which is complementary to the 3' ends of the double stranded DNA containing an entire region of the lysC gene or a segment thereof. If only a portion of the lysC gene is to be amplified, the gene library must be screened for DNA fragments containing the entire region, using the DNA fragment as the primer. If the entire region is to be amplified, the DNA fragment may be subjected to agarose gel electrophoresis, and then the desired band is cut out to recover the DNA fragment containing the lysC gene.

The DNA primer may be appropriately prepared based on, for example, a known sequence of *E. coli* (Cassan, M., Parsot, C., Cohen, G. N. and Patte J. C., J. Biol. Chem., 261, 1052, 1986), and preferred are the two types of primers, 5'-CTTCCCTTGTGCCAAGGCTG-3' (SEQ ID NO: 8) and 5'-GAATTCCTTTGCGAGCAG-3' (SEQ ID NO: 9) which are capable of amplifying the 1347-base region coding for the lysC gene. The synthesis of the DNA may be carried out in a conventional manner, using a DNA synthesizer model 380B, produced by Applied Biosystems Co., and the phosphoamidite method (see Tetrahedron Letters, 22, 1859, 1981). The PCR reaction may be carried out using a DNA thermal cycler Model PJ2000, produced by Takara Shuzo Co., and Taq DNA polymerase, produced by Takara Shuzo Co., by the method indicated by the supplier.

The lysC gene which has been amplified by the PCR method is linked to a vector DNA which is capable of replication in Escherichia bacteria, and the recombinant vector DNA is introduced into cells thereof. The method of transforming a host with the vector DNA to be used and the method of the confirming the presence of lysC are the same as those described previously.

The method of inducing mutations into the obtained lysC, such as the substitution, insertion or deletion of amino acids, may be effected by the recombinant PCR method (Higuchi, R., 61, PCR Technology (Erlich, H. A. Eds., Stockton Press, 1989)), the site-directed mutagenesis method (Kramer, W. and Frits, H. J. Meth. in Enzymol., 154, 350, 1987; Kunkel, T. A. et al. Meth. in Enzymol., 154, 367, 1987), etc. By using these methods, a desired mutation may be induced at a desired site. Furthermore, for the introduction of random mutation may be used a method of directly treating the object gene on chromosome DNA or a plasmid with hydroxylamine (Hashimoto, T. and Sekiguchi, M., J. Bacteriol., 159, 1039, 1984); a conventional method involving exposure of cells containing the object DNA to ultraviolet rays or to treatment with a chemical agent such as N-methyl-N'-nitro-N-nitrosoguanidine, nitrous acid, or the like; or a method of chemically synthesizing the object gene.

The method of selecting the inhibition-releasing mutant gene lysC* involves, at first, transforming with the mutated recombinant DNA an AK-deficient strain, for example, *E, coli* GT3 strain. Next, the transformant is cultured in a minimal medium, for example, M9, containing a significant amount of lysine. The strains which possess plasmids having the wild type of lysC exhibit the inhibition by lysine of AKIII which is the only AK in the strain, and therefore the synthesis of threonine, isoleucine, methionine and diaminopimeric acid (DAP) is no longer possible and growth is inhibited. In contrast, the strains which possess plasmids having lysC* which releases the inhibition by lysine should be capable of growing on a minimal medium containing a significant amount of lysine. Utilizing this phenomenon, the desired strains, that is, strains with plasmids having the lysC* which releases the inhibition, i.e., those which are resistant to lysine or to S-2-aminoethylcysteine (AEC), an analogue of lysine, may be selected.

The above mentioned mutant gene obtained in this manner may be used as the recombinant DNA for introduction into an appropriate microorganism (host) and expressed therein to obtain a microorganism possessing AK with release of the feedback inhibition.

The above mentioned wild strains of Escherichia bacteria may be mentioned as hosts into which the obtained lysC gene or mutant lysC gene (lysC*) is to be introduced and then amplified for the production of threonine, but in addition to these, any other bacteria may be used as hosts provided that both the replication origin of the recombinant vector DNA constructed here and the lysC gene or the mutated lysC gene (lysC*) function therein, the recombinant vector DNA is capable of replication therein, and the lysC gene or the mutated lysC gene (lysC*) may be reinforced therein. The most preferable host is *E. coli* B-3996 strain.

3. Preparation of L-Isoleucine by the Present Invention

According to the present invention, L-isoleucine can be prepared in good efficiency by cultivating a bacterium belonging to the genus Escherichia which is transformed by incorporating the released type thrABC operon prepared above and which further carries the released type ilvGMEDA operon in a suitable medium to thus produce L-isoleucine and accumulate it in the culture medium and then isolating L-isoleucine from the culture medium. More specifically, L-isoleucine can be prepared in good efficiency by incorporating, into a bacterium belonging to the genus Escherichia, the released type thrABC operon and the released type ilvGMEDA operon.

Moreover, L-isoleucine can be prepared in further improved efficiency by cultivating a bacterium belonging to the genus Escherichia which is transformed by incorporating the released type thrABC operon prepared above and which further carries the completely released type ilvGMEDA operon in a suitable medium to thus produce L-isoleucine and accumulate it in the culture medium and then isolating L-isoleucine from the culture medium. More specifically, L-isoleucine can be prepared in further improved efficiency by incorporating, into a bacterium belonging to the genus Escherichia, the released type thrABC operon and the completely released type ilvGMEDA operon.

Examples of the bacteria belonging to the genus Escherichia which carry the released type thrABC operon include those which are transformed by incorporating a DNA comprising the released type thrABC operon into the chromosomal DNA's thereof or those which are transformed by incorporating, into the bacterial cells, a recombinant DNA obtained by ligating the DNA with a vector DNA capable of undergoing automonous replication in the bacterial cells belonging to the genus Escherichia.

On the other hand, the transformation of a bacterium belonging to the genus Escherichia by incorporating a DNA comprising the released type ilvGMEDA operon into the bacterial cells may be carried out by incorporating the DNA comprising the released type ilvGMEDA operon into the chromosomal DNA thereof; or by incorporating, into the bacterial cells, a recombinant DNA obtained by ligating the DNA with a vector DNA capable of undergoing automonous replication in the bacterial cells belonging to the genus Escherichia.

Moreover, the transformation of a bacterium belonging to the genus Escherichia by incorporating a DNA comprising the completely released type ilvGMEDA operon into the bacterial cells may be carried out by incorporating the DNA comprising the completely released type ilvGMEDA operon into the chromosomal DNA thereof; or by incorporating, into the bacterial cells, a recombinant DNA obtained by ligating a DNA comprising the completely released type ilvGMEDA operon with a vector DNA capable of undergoing automonous replication in the bacterial cells belonging to the genus Escherichia.

If both of the released type thrABC operon and the released type ilvGMEDA operon or both of the released type thrABC operon and the completely released type ilvGMEDA operon are incorporated into a bacterium belonging to the genus Escherichia, these operons may be present in the bacterium in the form of the chromosomal DNA of the bacterium in which they are incorporated or may be present on a single plasmid or separate plasmids, i.e., in the form of a non-chromosomal DNA or DNA's. Moreover, one of these operons is incorporated into the chromosomal DNA of the bacterium and the other operon is incorporated in a plasmid present in the bacterium in the form of a non-chromosomal DNA. If the released type thrABC operon and the released type ilvGMEDA operon or the completely released type ilvGMEDA operon are transferred into a bacterium belonging to the genus Escherichia in the form of separate plasmids, they preferably have different replication origins so that these two plasmids do not show incompatibility with one another.

When a DNA comprising the released type thrABC operon and a DNA comprising the released type ilvGMEDA operon are transferred into a bacterium belonging to the genus Escherichia, they may be introduced thereinto in any order.

When a DNA comprising the released type thrABC operon and a DNA comprising the completely released type ilvGMEDA operon are transferred into a bacterium belonging to the genus Escherichia, they may be introduced thereinto in any order.

Any bacteria belonging to the genus Escherichia capable of undergoing replication through the function of the replication origin of a vector DNA used for incorporation within the bacterial cells can be used as the hosts when promoters of the released type thrABC operon, released type ilvGMEDA operon and completely released type ilvGMEDA operon or other promoters for expressing these genes fulfill their functions within the bacterial cells and either of these operons is incorporated into a plasmid in the form of a non-chromosomal DNA. On the other hand, if the released type thrABC operon, released type ilvGMEDA operon and completely released type ilvGMEDA operon are incorporated into a bacterium belonging to the genus Escherichia in the form of separate plasmids, both of the replication origins must fulfill the functions.

In the present invention, the production of L-isoleucine through the use of microorganisms may be carried out by the commonly used method for culturing microorganisms.

The mediums used in the cultivation may be synthetic or natural ones so far as they comprise carbon and nitrogen sources and inorganic substances as well as optional nutrients required for the growth of strains used.

Examples of carbon sources include various kinds of carbohydrates represented by glucose and various kinds of organic acids represented by pyruvic acid. In addition, alcohols such as ethanol and glycerin may be used depending on the assimilation ability of microorganisms used.

Examples of nitrogen sources include ammonia, various kinds of ammonium salts such as ammonium sulfate, amines and other nitrogen atom-containing compounds, and natural nitrogen sources such as peptone, soybean hydrolyzates and decomposed products of fermented bacterial cells.

Examples of inorganic substances are potassium primary phosphate, magnesium sulfate, sodium chloride, ferrous sulfate, manganese sulfate and calcium carbonate.

The cultivation of the microorganisms may be carried out under aerobic culture conditions such as shaking culture and aeration-agitation culture and the cultivation temperature ranges from 20 to 40° C., preferably 30 to 38° C. The pH value of the culture medium ranges from 5 to 9 and preferably 6.5 to 7.2. The pH of the culture medium is adjusted by addition of, for instance, ammonia, calcium carbonate, various acids, various bases and buffer solutions.

In general, a sufficient amount of L-isoleucine is accumulated in the culture medium by carrying out the cultivation for 1 to 3 days.

After the completion of the cultivation, solid contents such as bacterial cells are removed from the culture medium through centrifugation or separation through a membrane and then the culture medium is treated by, for instance, ion-exchange, concentration and/or crystallization methods to thus recover L-isoleucine.

The present invention will hereunder be described in more detail with reference to the following non-limitative working Examples.

Example 1

Construction of Plasmid pMWD5

The chromosomal DNA of *Escherichia coli* MI162 strain was isolated. Then the chromosomal DNA was digested with restriction enzyme HindIII. It has been proved that the HindIII-HindIII DNA fragment comprising the ilvGM gene has a length of 4.8 kb. Therefore, the HindIII-HindIII DNA fragment having a length of about 4.8 kb was ligated with a DNA fragment obtained by digesting the plasmid vector pBR322 purchased from Takara Shuzo Co., Ltd. with HindIII. The resulting DNA mixture was transferred into *Escherichia coli* MI262 strain which was defective in aceto- hydroxylic acid synthase activity. The strain whose phenotypic defect, i.e., defect in the expression of acetohydroxylic acid synthase was compensated through the transformation was selected, followed by isolating the plasmid possessed by the strain. The structure of the plasmid was analyzed and it was found that the plasmid comprised the ilvGM gene-containing DNA fragment having a length of 4.8 kb inserted at the HindIII site of the plasmid pBR322. The plasmid is herein referred to as "pBRGM711".

Oligonucleotide DNA's having base sequences of SEQ ID No: 4 SEQ ID No: 5 in the Sequence Listing were synthesized with reference to the base sequences reported in Gene, 1991, 97, p. 21, Proc. Natl. Acad. Sci. U.S.A., 1981, 78, p. 922 and J. Bacteriol., 1982, 149, p. 294. These DNA's were used as the primers in the DNA amplification by the PCR method while using the chromosomal DNA of the MI162 strain as a template. The DNA fragment amplified by the PCR method is the DNA fragment having a base sequence extending from 25th to 952th bases of SEQ ID No. 1 in the Sequence Listing. The DNA fragment is hereunder referred to as "fragment (A)".

In the same manner, oligonucleotide DNA's having base sequences of SEQ ID No: 6 and SEQ ID No: 7 in the Sequence Listing were synthesized with reference to the base sequences reported in Gene, 1991, 97, p. 21, Proc. Natl. Acad. Sci. U.S.A., 1981, 78, p. 922 and J. Bacteriol., 1982, 149, p. 294. These DNA's were used as the primers in the DNA amplification by the PCR method while using the chromosomal DNA of the MI162 strain as a template. The DNA fragment amplified by the PCR method is the DNA fragment having a base sequence extending from 1161th to 2421th bases of the sequence of SEQ ID No. 1 in the Sequence Listing. The DNA fragment is hereunder referred to as "fragment (B)".

A large DNA fragment obtained by digesting the fragment (A) with SmaI was ligated with a DNA fragment obtained by digesting a plasmid pUC18 (available from Takara Shuzo Co., Ltd.) with SmaI to construct a plasmid pUCA. A large fragment obtained by digesting the fragment (B) with KpnI was ligated with a large fragment obtained by digesting a plasmid pHSG399 (available from Takara Shuzo Co., Ltd.) with HincII and KpnI to construct a plasmid pHSGB.

The plasmid pUCA was digested with KpnI, the incised ends were converted into blunt ends using a large fragment (Klenow fragment) of DNA polymerase I, followed by digesting with PstI to finally isolate a DNA fragment comprising the fragment (A). Separately, the plasmid pHSGB was digested with HindIII, the incised ends were converted into blunt ends using a large fragment (Klenow fragment) of DNA polymerase I, followed by digesting with PstI to finally isolate a DNA fragment comprising the fragment (B). The DNA fragments thus prepared were ligated to give a plasmid pHSGSK.

The SmaI-KpnI fragment originated from the fragments (A) and (B) and possessed by the plasmid pHSGSK is herein referred to as "fragment (C)". The fragment (C) corresponds to one obtained by incising the ilvGM gene-containing HindIII—HindIII fragment having a length of 4.8 kb with SmaI and KpnI and comprises a promoter, an SD sequence and the upstream region of the ilvG gene, but lacks the sequence extending from the leader sequence to the attenuator region, i.e., a sequence of about 0.2 kb. The foregoing procedures for constructing the plasmid pHSGSK are summarized in FIG. 1.

The plasmid pHSGSK was digested with SmaI and KpnI to give the fragment (C), separately the plasmid pBRGM7 was digested with SmaI and KpnI to give a large DNA fragment and these fragments were ligated. The resulting plasmid is hereunder referred to as "pdGM1". The ilvGM gene-containing HindIII—HindIII fragment of 4.6 kb which is possessed by the plasmid pdGM1 lacks the region required for the attenuation. The ilvGM gene lacking the region required for the attenuation is expressed by "ΔattGM" in this Example and attached figures. The foregoing procedures for constructing the plasmid pdGM1 are summarized in FIG. 2.

The plasmid pDRIA4 disclosed in J.P. KOKAI No. Hei 2-458 can be prepared by ligating a shuttle vector pDR1120 which is capable of undergoing automonous replication in the bacteria belonging to the genus Escherichia and those belonging to the genus Brevibacterium, with a BamHI—BamHI fragment comprising the ilvA gene coding for threonine deaminase substantially released from the inhibition by L-isoleucine. Incidentally, J.P. KOKAI No. Hei 2-458 discloses that the BamHI—BamHI fragment has a length of 2.3 kb, but it has presently been proved that it has a length of 2.75 kb. The plasmid pDRIA4 is present in the non-chromosomal DNA of Brevibacterium flavum AJ12358 (FERM BP-5087) and Brevibacterium flavum AJ12359 (FERM BP-5088). AJ 12358 and AJ 12359 were deposited with the National Industrial Bioscience and Human-Technology Agency of Industrial Science and Technology, 1-3, Higashi 1-chome, Tsukuba-shi, Ibaraki-Ken 305, Japan, on Dec. 16, 1987, and can be accessed under the identification numbers FERM BP-5087 and FERM BP-5089, respectively. The plasmid pDRIA4 can be prepared from these strains by the usual method.

There was prepared the HindIII-BamHI fragment comprising the ilvA gene coding for threonine deaminase substantially released from the inhibition by L-isoleucine, out of the BamHI—BamHI DNA fragments having a length of 2.3 kb and present on the plasmid pDRIA4, followed by ligating the fragment with a DNA fragment obtained by incising the vector pMW119 (available from Nippon Gene Co., Ltd.) with HindIII and BamHI. The plasmid thus constructed is named "pMWA1". The ilvA gene coding for threonine deaminase substantially released from the inhibition by L-isoleucine is sometimes expressed by "A*" in this Example and the attached figures.

The DNA fragment obtained by incising the plasmid pMWA1 with HindIII was ligated with the ilvGM gene-containing DNA fragment obtained by incising the plasmid pdGM1 with HindIII. The positions of restriction enzyme-recognizing sites present on the resulting plasmids were analyzed to thus select a plasmid whose transcriptional direction of the ilvGM gene was in agreement with that of the ilvA gene and the plasmid thus selected is named "pMWGMA2". The foregoing procedures for constructing the plasmid pMWGMA2 are summarized in FIG. 3.

The chromosomal DNA of the *Escherichia coli* MI162 strain was prepared and incised with SalI and PstI to prepare a mixture of DNA fragments. On the other hand, the vector pUC19 (available from Takara Shuzo Co., Ltd.) was incised with SalI and PstI to prepare a DNA fragment. The DNA fragment mixture was ligated with the DNA fragment obtained by incising the vector pUC119 to give a DNA mixture. The DNA mixture was transferred into the AB2070 strain defective in transaminase B activity, followed by selecting a strain whose requirement for branched amino acids was regenerated through the transformation. A plasmid was prepared from the strain and it was found that the DNA fragment obtained by incising the plasmid pUC19 with SalI and PstI was ligated with the ilvE gene-containing SalI-PstI DNA fragment in this plasmid. The plasmid is named "pUCE1".

The plasmid pMWGMA2 was partially digested with HindIII to prepare a DNA fragment mixture. On the other hand, the plasmid pUCE1 was incised with HindIII to prepare a HindIII—HindIII DNA fragment of 1.7 kb comprising a part of the ilvE gene and a part of the ilvD gene. The AB1280 strain defective in dihydroxylic acid dehydratase (product coded by the ilvD gene) activity was transformed using the DNA mixture obtained by ligating these DNA fragment and fragment mixture, followed by selecting a strain which lost the requirement for branched amino acid from the transformed strains. A plasmid was prepared from the transformed strain and it was found that the DNA fragment obtained through incision of the plasmid pMWGMA2 only at the HindIII site present between ΔattGM and A* was ligated with the HindIII—HindIII DNA fragment of 1.7 kb comprising a part of the ilvE gene originated from the plasmid pUCE1 and a part of the ilvD gene and that the ilvGMEDA operon was regenerated. The plasmid thus prepared is named "pMWD5". The foregoing procedures for constructing the plasmid pMWD5 are summarized in FIG. 4.

The plasmid pMWD5 thus prepared comprises the plasmid pMW119 as a vector and is thus a plasmid carrying the ilvGMEDA operon which comprises the ilvA gene coding for TD substantially released from the inhibition by L-isoleucine and from which the region required for the attenuation is removed.

EXAMPLE 2

Construction of L-Isoleucine-Producing Strain

The plasmid pMWD5 prepared in Example 1 was transferred to the L-threonine-producing bacterium, i.e., *Escherichia coli* B-3996 strain disclosed in J.P. KOKAI No. Hei 3-501682 and U.S. Pat. No. 5,175,107 by the usual method, i.e., the rubidium chloride method. A transformant which was resistant to both 100 $\mu$g/ml of Streptomycin and 100 $\mu$g/ml of Ampicillin was selected from the strains transformed with the plasmid pMWD5. The resulting transformant is named "AJ12919".

The L-threonine-producing bacterium, i.e., *Escherichia coli* B-3996 strain was deposited with the former USSR Antibiotics Research Institute under on Nov. 19, 1990 the accession number of 1867. The host strain of the B-3996 strain is *Escherichia coli* TDH-6 strain which is defective in the thrC gene, has a saccharose-assimilation ability, can proliferate in the presence of 5 mg/ml of L-threonine and is defective in threonine dehydrogenase activity and whose ilvA gene possesses a leaky mutation. The B-3996 strain carries a plasmid pVIC40 obtained by loading the thrABC operon which comprises the thrA gene coding for AKI-HDI substantially released from the inhibition by L-threonine on a vector derived from a vector RSF1010 having a broad-spectrum with respect to host. Therefore, the Escherichia coli AJ12919 strain carrying the plasmid pVIC40 and the plasmid pMWD5 is a strain carrying, through the plasmid vectors, the thrABC operon which comprises the thrA gene coding for AKI-HDI substantially released from the inhibition by L-threonine and the ilvGMEDA operon which comprises the ilvA gene coding for TD substantially released from the inhibition by L-isoleucine and from which the region required for the attenuation is removed.

EXAMPLE 3

Test (1) for Producing L-Isoleucine Using AJ12919 Strain

A test for producing L-isoleucine through fermentation by the AJ12919 strain constructed in Example 2 was performed. The AJ12919 strain was smeared on a medium comprising 1% bactotrypsin, 0.5% yeast extract, 0.5% NaCl, 1.5% agar, 100 μg/ml Streptomycin and 100 μg/ml Ampicillin, followed by cultivation at a temperature of 37° C. for 18 to 24 hours, inoculation, with a platinum loop, of a part of the culture medium on 20 ml of a fermentation medium (4% glucose, 1.6% ammonium sulfate, 0.1% potassium dihydrogen phosphate, 0.1% magnesium sulfate heptahydrate, 0.001% ferrous sulfate heptahydrate, 0.001% manganese sulfate pentahydrate, 0.2% yeast extract, 3% calcium carbonate, pH 7.0) and cultivation at 37° C. for 24 hours by the shaking culture method. After removing the bacterial cells, the resulting culture supernatant was inspected for the concentrations of L-isoleucine and L-threonine present therein by the high performance liquid chromatography. The results thus obtained are listed in the following Table 1.

TABLE 1

| Strain | L-Isoleucine Concn.(g/l) | L-Threonine Concn.(g/l) |
|---|---|---|
| AJ129191 | 10 | 0 |

EXAMPLE 4

Test (2) for Producing L-Isoleucine Using AJ12919 Strain

After cultivating the strain AJ12919 at 37° C. for 24 hours in an agar medium identical to that used in Example 3, the culture medium was inoculated on a 300 ml of a fermentation medium having a composition identical to that used in Example 3 and contained in a one liter volume fermenter, followed by cultivation at a stirring speed of 400 rpm, a quantity of airflow of 300 ml/min and at a temperature of 37° C. for 16 hours to give a seed culture medium. The resulting seed culture medium (30 ml) was inoculated on 250 ml of a fermentation medium comprising 6% glucose, 1.6% ammonium sulfate, 0.1% potassium dihydrogen phosphate, 0.1% magnesium sulfate heptahydrate, 0.001% ferrous sulfate heptahydrate, 0.001% manganese sulfate pentahydrate and 0.2% yeast extract (pH 7.0) contained in a one liter volume fermenter, followed by cultivation at 37° C., a quantity of airflow of 300 ml/min for 23 hours while controlling the stirring speed such that the concentration of dissolved oxygen in the culture medium was not less than 5%, properly supplying glucose and maintaining the pH level at about 7.0 through the addition of ammonia gas. After removing the bacterial cells, the resulting culture supernatant was inspected for the concentration of L-isoleucine present therein by the high performance liquid chromatography. As a result, it was found that 39 g/l of L-isoleucine was accumulated in the culture supernatant.

EXAMPLE 5

Construction of L-Isoleucine-Producing Strain (2)

PCT WO94/11517 discloses a method for constructing a plasmid pVICLC*80A in which a vector derived from a vector RSF1010 having a broad-spectrum with respect to host carries a thrABC operon comprising a thrA gene coding for AKI-HDI substantially released from the inhibition by L-threonine and a lysC gene coding for AKIII substantially released from the inhibition by L-lysine, from the plasmid pVIC40 present in the L-threonine-producing bacterium B-3996 strain deposited with the former USSR Antibiotics Research Institute under the accession No. 1867 and the plasmid pLLC*80 carrying the lysC gene coding for AKIII substantially released from the inhibition by L-lysine and deposited with National Institute of Bioscience and Human-Technology Agency of Industrial Science and Technology under the accession number of FERM BP-4462, as well as an L-threonine-producing bacterium which is obtained by transferring the plasmid pVICLC*80A into a B-399 strain (TDH-6 strain) which is the host for the strain B-3996.

The plasmid pMWD5 prepared in Example 1 was transferred into the L-threonine-producing bacterium obtained by transferring the plasmid pVICLC*80A into a B-399 strain (TDH-6 strain) as the host for the strain B-3996 according to the usual method, i.e., the rubidium chloride method. A transformant which was resistant to both 100 μg/ml of Streptomycin and 100 μg/ml of Ampicillin was selected from the strains transformed with the plasmid pMWD5. The resulting transformant is named "AJ 13100 strain".

The host microorganism for the AJ 13100 strain is *Escherichia coli* TDH-6 strain (B-399 strain) which is defective in the thrC gene, has a saccharose-assimilation ability, can proliferate in the presence of 5 mg/ml of L-threonine and is defective in threonine dehydrogenase activity and whose ilvA gene possesses a leaky mutation. The AJ 13100 strain carries the plasmid pVICLC*80A obtained by loading the thrABC operon which comprises the thrA gene coding for AKI-HDI substantially released from the inhibition by L-threonine and the lysC gene coding for AKIII substantially released from the inhibition by L-lysine on a vector derived from a vector RSF1010 having a broad-spectrum with respect to host, as well as the plasmid pMWD5 prepared in Example 1. Therefore, the *Escherichia coli* AJ 13100 strain is a strain carrying, through the plasmid vectors, the thrABC operon which comprises the thrA gene coding for AKI-HDI substantially released from the inhibition by L-threonine and the ilvGMEDA operon which comprises the LysC gene coding for AKIII substantially released from the inhibition by L-lysine and the ilvA gene coding for TD substantially released from the inhibition by L-isoleucine and from which the region required for the attenuation is removed.

EXAMPLE 6

Test for Producing L-Isoleucine Using AJ 13100 Strain

A test for producing L-isoleucine through fermentation by the AJ 13100 strain constructed in Example 5 was performed. The AJ 13100 strain was smeared on a medium comprising 1% bactotrypsin, 0.5% yeast extract, 0.5% NaCl, 1.5% agar, 100 μg/ml Streptomycin and 100 μg/ml Ampicillin, followed by cultivation at a temperature of 37° C. for 18 to 24 hours, inoculation, with a platinum loop, of a part of the culture medium on 20 ml of a fermentation medium (4% glucose, 1.6% ammonium sulfate, 0.1% potassium dihydrogen phosphate, 0.1% magnesium sulfate heptahydrate, 0.001% ferrous sulfate heptahydrate, 0.001% manganese sulfate pentahydrate, 0.2% yeast extract, 3% calcium carbonate, pH 7.0) and cultivation at 37° C. for 24 hours by the shaking culture method. Separately, the AJ12919 strain was also cultured in the same manner. After removing the bacterial cells, each culture supernatant thus obtained was inspected for the concentrations of L-isoleucine and L-threonine present therein by the high performance liquid chromatography. The results thus obtained are listed in the following Table 2.

TABLE 2

| Strain | L-Isoleucine Concn.(g/l) | L-Threonine Concn.(g/l) |
|---|---|---|
| AJ12919 | 10 | 0 |
| AJ13100 | 12 | 0 |

In the L-isoleucine-producing bacterium belonging to the genus Escherichia according to the present invention, the thrABC operon comprising the thrA gene coding for aspartokinase I-homoserine dehydrogenase I substantially released from the inhibition by L-threonine is loaded on a plasmid of multiple copy number and amplified and therefore, the bacterium permits biosynthesis of a sufficient amount of L-threonine as the precursor of L-isoleucine. Moreover, the ilvGMEDA operon which comprises the ilvA gene coding for threonine deaminase substantially released from the inhibition by L-isoleucine and from which the region required for the attenuation is removed is loaded on a plasmid of multiplecopy and amplified in the bacterium and therefore, the bacterium can efficiently convert L-threonine into L-isoleucine.

The use of the ilvGMEDA operon which comprises the ilvA gene coding for threonine deaminase substantially released from the inhibition by L-isoleucine and from which the region required for the attenuation is removed permits well-balanced production of a group of enzymes involved in the L-isoleucine biosynthesis system and derived from the ilvGM gene, ilvE gene, ilvD gene and ilvA gene. The transcription highly efficiently takes place since it is performed by the primary promoter.

In general, it would be concluded that the negative control for the transcription level of the ilvGMEDA operon is released simply by increasing the quantity of genes of the ilvGMEDA operon comprising the ilvA gene coding for threonine deaminase substantially released from the inhibition by L-isoleucine through the use of a plasmid of multiple copy number and that the productivity of L-isoleucine is satisfactorily improved, while the present invention has unexpectedly succeeded in further improvement of the productivity of L-isoleucine by removing the region required for the attenuation in addition to the foregoing operation.

What is claimed is:

1. An L-isoleucine-producing bacterium belonging to the genus Escherichia carrying a thrABC operon which comprises a thrA gene coding for aspartokinase I-homoserine dehydrogenase I released from the inhibition by L-threonine and an ilvGMEDA operon which comprises an ilvA gene coding for threonine deaminase released from the inhibition by L-isoleucine and whose region required for attenuation is removed, wherein the bacterium belonging to the genus Escherichia is *Escherichia coli*, said thrABC operon is the *Escherichia coli* thrABC operon, and said ilvGMEDA operon is the *Escherichia coli* ilvGMEDA operon.

2. The bacterium belonging to the genus Escherichia of claim 1, wherein the bacterium comprises two kinds of plasmids, one of which is a plasmid (A) carrying the thrABC operon and the other of which is a plasmid (B) carrying the ilvGMEDA operon.

3. The bacterium belonging to the genus Escherichia of claim 1, wherein the thrABC operon and the ilvGMEDA operon are carried on a plasmid or plasmids.

4. The bacterium belonging to the genus Escherichia of claim 3, wherein the bacterium comprises two kinds of plasmids, one of which is a plasmid (A) carrying the thrABC operon and the other of which is a plasmid (B) carrying the ilvGMEDA operon.

5. The bacterium belonging to the genus Escherichia of claim 1, wherein the ilvGMEDA operon is one having a DNA sequence of SEQ ID No. 1 in the Sequence Listing which is lacking in the sequence extending from 953rd base to 1160th base.

6. The bacterium belonging to the genus Escherichia of claim 4, wherein the plasmid (A) is a plasmid pVIC40 and the plasmid (B) is a plasmid pMWD5.

7. The bacterium belonging to the genus Escherichia of claim 1, wherein the thrABC operon and the ilvGMEDA operon are introduced into a host strain which is defective in thrC gene, can proliferate in the presence of 5 mg/ml of L-threonine, is defective in threonine dehydrogenase activity and has a leaky mutation in the ilvA gene.

8. The bacterium belonging to the genus Escherichia of claim 7, wherein it is *Escherichia coli* AJ12919 strain.

9. A method for preparing L-isoleucine through fermentation comprising the steps of cultivating, in a culture medium, a bacterium belonging to the genus Escherichia of claim 1, and then recovering L-isoleucine formed and accumulated in the medium.

10. An L-isoleucine-producing bacterium belonging to the genus Escherichia carrying a thrABC operon which comprises a thrA gene coding for aspartokinase I-homoserine dehydrogenase I released from the inhibition by L-threonine, an lysC gene coding for aspartokinase III released from the inhibition by L-lysine, and an ilvGMEDA operon which comprises an ilvA gene coding for threonine deaminase released from the inhibition by L-isoleucine and whose region required for attenuation is removed, wherein the bacterium belonging to the genus Escherichia is *Escherichia coli*, said thrABC operon is the *Escherichia coli* thrABC operon, said ilvGMEDA operon is the *Escherichia coli* ilvGMEDA operon, and said lysC gene is the *Escherichia coli* lysC gene.

11. The bacterium belonging to the genus Escherichia of claim 10, wherein it carries two kinds of plasmids, one of which is a plasmid (C) carrying the thrABC operon and the lysC gene and the other of which is a plasmid (B) carrying the ilvGMEDA operon.

12. The bacterium belonging to the genus Escherichia of claim 10, wherein the thrABC operon, the lysC gene and the ilvGMEDA operon are carried on a plasmid or plasmids.

13. The bacterium belonging to the genus Escherichia of claim 12, wherein it carries two kinds of plasmids, one of which is a plasmid (C) carrying the thrABC operon and the lysC gene and the other of which is a plasmid (B) carrying the ilvGMEDA operon.

14. The bacterium belonging to the genus Escherichia of claim 10, wherein the ilvGMEDA operon is one having a DNA sequence of SEQ ID No. 1 in the Sequence Listing which is lacking in the sequence extending from 953rd base to 1160th base.

15. The bacterium belonging to the genus Escherichia of claim 10, wherein the thrABC operon, the lysC gene and the ilvGMEDA operon are introduced into a host strain which is defective in thrC gene, has an ability of assimilating saccharose, can proliferate in the presence of 5 mg/ml of L-threonine, is defective in threonine dehydrogenase activity and has a leaky mutation in the ilvA gene.

16. A method for preparing L-isoleucine through fermentation comprising the steps of cultivating, in a culture medium, a bacterium belonging to the genus Escherichia of claim 10, and then recovering L-isoleucine formed and accumulated in the medium.

\* \* \* \* \*